United States Patent
Yu et al.

(10) Patent No.: US 9,284,611 B2
(45) Date of Patent: Mar. 15, 2016

(54) EPIGENETIC BIOMARKER ZNF545 FOR DIAGNOSING AND PROGNOSIS OF GASTRIC CANCER

(71) Applicant: The Chinese University of Hong Kong, Shatin, New Territories (CN)

(72) Inventors: Jun Yu, Lake Silver (CN); Joseph Jao Yiu Sung, Ma On san (CN)

(73) Assignee: The Chinese University of Hong Kong, Shatin, N.T., Hong Kong SAR (CN)

( * ) Notice: Subject to any disclaimer, the term of this patent is extended or adjusted under 35 U.S.C. 154(b) by 191 days.

(21) Appl. No.: 13/796,864

(22) Filed: Mar. 12, 2013

(65) Prior Publication Data

US 2014/0274753 A1    Sep. 18, 2014

(51) Int. Cl.
| | |
|---|---|
| *C12Q 1/68* | (2006.01) |
| *C12N 15/113* | (2010.01) |
| *C07K 14/47* | (2006.01) |
| *G01N 33/574* | (2006.01) |
| *A61K 38/17* | (2006.01) |

(52) U.S. Cl.
CPC .......... *C12Q 1/6886* (2013.01); *A61K 38/1709* (2013.01); *C07K 14/47* (2013.01); *C12N 15/113* (2013.01); *G01N 33/57446* (2013.01); *C12N 2310/14* (2013.01); *C12Q 2600/118* (2013.01); *C12Q 2600/154* (2013.01); *C12Q 2600/158* (2013.01)

(58) Field of Classification Search
None
See application file for complete search history.

(56) References Cited

FOREIGN PATENT DOCUMENTS

WO    2007/143037 A2    12/2007

OTHER PUBLICATIONS

Kim et al. (2004) Methylation of RUNX3 in various types of human cancers and premalignant stages of gastric carcinoma. Laboratory Investigation, 84:479-484.*
Cheng et al. (2010) Proceedings: AACR 101st Annual Meeting, Apr. 17-21, 2010, Abstract 197: The KRAB-containing zinc finger protein ZNF545 is a functional tumor suppressor exerting proapoptotic and antiproliferation abilities with frequent epigenetic inactivation in multiple carcinomas.*
NCBI Reference Accession NC_000019.9, GI:224589810, *Homo sapiens* chromosome 19, GRCh37.p5 Primary Assembly, priority to Jul. 29, 2011, 3 pages.*
Cheng et al. (2012) A Novel 19q13 Nucleolar Zinc Finger Protein Suppresses Tumor Cell Growth through Inhibiting Ribosome Biogenesis and Inducing Apoptosis but Is Frequently Silenced in Multiple Carcinomas. Molecular Cancer Research, 10(7):925-936.*
Wang et al. (2012) Zinc-finger protein 545 is a novel tumour suppressor that acts by inhibiting ribosomal RNA transcription in gastric cancer. Gut, 62:833-841.*
Cheng et al. (2012) A Novel 19q13 Nucleolar Zinc Finger Protein Suppresses Tumor Cell Growth through Inhibiting Ribosome Biogenesis and Inducing Apoptosis but Is Frequently Silenced in Multiple Carcinomas. Molecular Cancer Research, 10(7):925-936, and Supplementary Figures 1-3 and Tables 1 and 2.*
Davies, C. "Methylation-Sensitive Restriction Fingerprinting", in Mills et al., "Methods in Molecular Biology: DNA methylation Protocols", vol. 200, Totowa:Humana Press, 2002. pp. 43-51.*
Du et al., "ADAMTS9 is a functional tumor suppressor through inhibiting AKT/mTOR pathway and associated with poor survival in gastric cancer", Oncogene, vol. 32, pp. 3319-3328 (2012).
Zhang et al., "High-resolution melting analysys of *ADAMTS9* methylation levels in gastric, colorectal, and pancreatic cancers", Cancer Genetics and Cytogenetics, vol. 196, pp. 38-44 (2010).

* cited by examiner

Primary Examiner — Michele K Joike
Assistant Examiner — Neil P. Hammell
(74) Attorney, Agent, or Firm — Kilpatrick Townsend & Stockton LLP

(57) ABSTRACT

The present invention provides a method for diagnosing and determining prognosis of gastric cancer in a subject by detecting suppressed expression of the ZNF545 gene, which in some cases is due to elevated methylation level in the genomic sequence of this gene. A kit and device useful for such a method are also provided. In addition, the present invention provides a method for treating gastric cancer by increasing ZNF545 gene expression or activity.

5 Claims, 10 Drawing Sheets

Figure 6.

| Variable | HR (95% CI) | p Value |
|---|---|---|
| Age | 1.01 (0.99 to 1.03) | 0.30 |
| Gender | | |
|   Male | 0.66 (0.41 to 1.04) | 0.07 |
|   Female | 1.00 | |
| *Helicobacter pylori* infection | | |
|   Negative | 0.90 (0.48 to 1.67) | 0.73 |
|   Positive | 1.00 | |
| Lauren | | |
|   Diffuse | 1.70 (0.97 to 2.97) | 0.06 |
|   Mixed | 0.83 (0.25 to 2.76) | 0.76 |
|   Intestinal | 1.00 | |
| Differentiation | | |
|   Well | 0.38 (0.90 to 1.59) | 0.19 |
|   Moderate | 1.00 (0.55 to 1.81) | 0.99 |
|   Poor | 1 | |
| TNM stage | | |
|   I | 0.24 (0.11 to 0.54) | 0.001 |
|   II | 0.21 (0.09 to 0.47) | <0.001 |
|   III | 0.40 (0.22 to 0.71) | 0.002 |
|   IV | 1.00 | |
| ZNF545 methylation in cancer tissues | | |
|   Methylated | 1.072 (0.673 to 1.803) | 0.80 |
|   Unmethylated | 1.00 | |
| ZNF545 methylation in adjacent non-tumour tissues | | |
|   Methylated | 2.28 (1.26 to 4.13) | 0.007 |
|   Unmethylated | 1.00 | |

TNM, tumour node metastases.

Figure 7.

| Variable | HR (95% CI) | p Value |
|---|---|---|
| Age | 1.00 (0.97 to 1.02) | 0.67 |
| Gender | | |
| Male | 0.42 (0.21 to 0.86) | 0.02 |
| Female | 1.00 | |
| TNM stage | | |
| I | 0.24 (0.09 to 0.61) | 0.003 |
| II | 0.22 (0.08 to 0.60) | 0.003 |
| III | 0.39 (0.17 to 0.86) | 0.021 |
| IV | 1.00 | |
| ZNF545 methylation in adjacent non-tumour tissues | | |
| Methylated | 2.01 (1.04 to 4.12) | 0.03 |
| Unmethylated | 1.00 | |

TNM, tumour node metastases.

Figure 8.

| | Primer Name | Sequence (5'-3') | Annealing temperature |
|---|---|---|---|
| | Methylation specific PCR | | |
| SEQ ID NO: 12 | ZNF545-MSP-MF | TTTTTTTTTAGGTTTTGTCGCGTC | 60 |
| SEQ ID NO: 13 | ZNF545-MSP-MR | CTACTAAAAAAACCGAACGCG | |
| SEQ ID NO: 14 | ZNF545-MSP-UF | TTTTTTTTTAGGTTTTGTTGTGTT | 58 |
| SEQ ID NO: 15 | ZNF545-MSP-UR | CCAAACACACTCACAAAATACA | |
| | Bisulfite genomic sequencing | | |
| SEQ ID NO: 16 | ZNF545-BGS-F | GTATAGGGTTTTTTAGTTGGTAT | 58 |
| SEQ ID NO: 17 | ZNF545-BGS-R | CCTCTCTCTTTACCCCCTAA | |
| | RT-PCR | | |
| SEQ ID NO: 6 | ZNF545-F | GAGCCTTGGAAAGTTGTGAG | 55 |
| SEQ ID NO: 7 | ZNF545-R | GGCATTTTCACACTACTGAAG | |
| SEQ ID NO: 8 | β-actin-F | GTCTTCCCCTCCATCGTG | 60 |
| SEQ ID NO: 9 | β-actin-R | AGGGTGAGGATGCCTCTCTT | |
| SEQ ID NO: 10 | HP1β-F | TGGTAAAGGGCAAAGTGGAG | 60 |
| SEQ ID NO: 11 | HP1β-R | GGGCAATCCAGGTTCTCTTC | |

Figure 9.

| Variable | Unmethylation (n = 38) | % | Methylation (n = 41) | % | P value |
|---|---|---|---|---|---|
| Age | | | | | |
| Mean ± SD | 64.03 ± 13.92 | | 65.41 ± 12.76 | | 0.65 |
| Gender | | | | | |
| M | 16 | 39.0% | 25 | 61.0% | 0.09 |
| F | 22 | 57.9% | 16 | 42.1% | |
| ***H. pylori* infection** | | | | | |
| Negative | 14 | 58.3% | 10 | 41.7% | 0.20 |
| Positive | 10 | 40.0% | 15 | 60.0% | |
| Lauren | | | | | |
| Diffuse or Mixed | 17 | 60.7% | 11 | 39.3% | 0.10 |
| Intestinal | 13 | 39.4% | 20 | 60.6% | |
| Differentiation | | | | | |
| Poor differentiation | 15 | 51.7% | 14 | 48.3% | 0.25 |
| Well or moderate | 9 | 36.0% | 16 | 64.0% | |
| TNM stage | | | | | |
| I-II | 13 | 54.2% | 11 | 45.8% | 0.44 |
| III-IV | 20 | 44.4% | 25 | 55.6% | |

Figure 10.

| Variable | Unmethylation (n = 54) | % | Methylation (n = 20) | % | P value |
|---|---|---|---|---|---|
| Age | | | | | |
| Mean ± SD | 65.07 ± 12.89 | | 71.25 ± 10.67 | | 0.06 |
| Gender | | | | | |
| M | 30 | 75.0% | 10 | 25.0% | 0.67 |
| F | 24 | 70.6% | 10 | 29.4% | |
| ***H. pylori* infection** | | | | | |
| Negative | 17 | 81.0% | 4 | 19.0% | 0.38 |
| Positive | 16 | 69.6% | 7 | 30.4% | |
| Lauren | | | | | |
| Diffuse or Mixed | 22 | 81.5% | 5 | 18.5% | 0.38 |
| Intestinal | 20 | 71.4% | 8 | 28.6% | |
| Differentiation | | | | | |
| Poor differentiation | 26 | 81.2% | 6 | 18.8% | 0.46 |
| Well or moderate | 16 | 72.7% | 6 | 27.3% | |
| Histology | | | | | |
| Precancerous lesion | 22 | 64.7% | 12 | 35.3% | 0.14 |
| Chronic gastritis | 32 | 80.0% | 8 | 20.0% | |
| TNM stage | | | | | |
| I-II | 20 | 76.9% | 6 | 23.1% | 0.54 |
| III-IV | 28 | 70.0% | 12 | 30.0% | |

SEQUENCE LISTING

<160> NUMBER OF SEQ ID NOS: 25

<210> SEQ ID NO 1
<211> LENGTH: 177
<212> TYPE: DNA
<213> ORGANISM: Homo sapiens
<220> FEATURE:
<221> NAME/KEY: promoter
<222> LOCATION: (1)...(177)
<223> OTHER INFORMATION: human ZNF545 gene promoter region (MSP region)

<400> SEQUENCE: 1 tccccteccag gccctgccgc gccgtcccca ggcgctaagg gactcgaagc gcagcctcgc     60
tgggacggac ctagctccgg ctccgggttc acgcagagca ggggctgcac cagcgagcgg    120 accccttgaga ctggccgcgc ctgcgcactc cgtgagcgcg cccggccctc ccagcag      177

<210> SEQ ID NO 2
<211> LENGTH: 428
<212> TYPE: DNA
<213> ORGANISM: Homo sapiens
<220> FEATURE:
<221> NAME/KEY: promoter
<222> LOCATION: (1)...(428)
<223> OTHER INFORMATION: human ZNF545 gene promoter region (BGS region),
      (positions -271 to +157 from transcription start site)

<400> SEQUENCE: 2
tcacagggct ccctagttgg cactatagag aggcggtcgc gggcgcccct ctttaacgcg      60
ccagccatct gtccccgctc ccctccaggc cctgccgcgc cgtcccagg cgctaaggga      120 ctcgaagcgc agcctcgctg ggacggacct agctccggct ccgggttcac gcagagcagg      180
ggctgcacca gcgagcggac ccttgagact ggccgcgcct gcgcactccg tgagcgcgcc      240
cggccctccc agcagcctcc gcgcgcagcc cgttaggccc cggggattgt ggcgtgaccc      300
ggcagcggct cctccgttc gggcatcgct gtgcctcggg ttcgcgcccc gagtgagcag      360
tcctggcccg gagcgtcggt cctggtaatc tgtaggaaaa gcgctgcggc ccaggggta      420 aagagagg                                                             428

<210> SEQ ID NO 3
<211> LENGTH: 1599
<212> TYPE: DNA
<213> ORGANISM: Homo sapiens
<220> FEATURE:
<223> OTHER INFORMATION: human zinc finger protein 545 (ZNF545), ZFP82
      zinc finger protein (ZFP82, zpf-82), zinc finger
      protein 85 coding region (CDS)
<220> FEATURE:
<221> NAME/KEY: CDS
<222> LOCATION: (1)...(1599)
<223> OTHER INFORMATION: human zinc finger protein 545 (ZNF545)

<400> SEQUENCE: 3 atggccctte gatcagtgat gttcagtgat gtatccatag acttctctcc agaagagtgg      60
gaatacctgg acttggaaca aaaggacttg tacagagatg tcatgttgga gaactacagc      120
aacttggtct cactgggatg cttcatttct aaaccagatg tgatttcctc attggagcaa      180
ggaaaagagc cttggaaagt tgtgaggaaa ggaagaagac aatatccaga tttggagacc      240
aagtatgaga ccaagaagtt atctttagaa aatgacattt atgaaataaa tttatcccag      300
tggaagataa tggaagaat tgaaaaccat ggccttaagg gtctcatttt aaaaaatgat      360
tgggaatcca caggaaaaat tgaaggacag gagagacctc aagaaggata cttcagtagt      420
gtgaaaatgc catctgaaaa ggtgtcctct taccagaaac gcacatcgt tactccacat      480 cagagacttc attttgttga taaaccctat gaatgtaagg aatgtgggaa ggcgttcaga      540
gtgcgccaac agcttacttt tcatcacaga attcatactg tgaaaaacc gtatgaatgt      600 aaggaatgtg ggatggcctt cagacagact gcacaccta ctcgacatca gagacttcat      660
tctggtgaaa aactctatga atgtaaggaa tgtggggaag cttctcatatg tggtgcagat      720 cttagagtac atcagaaaat gcatattggt gagaagccct atgaatgtaa agaatgtggg      780
aaggctttta gggtacgagg acaacttact ctgcatcaga ggattcatac tggtgagaaa      840
ccctatgtgt gtaaagagtg tggaaaagcc tttagacagt acgcacacct gactcggcat      900
cagaagctta atagtgctga caggctctat gaatgcaaag aatgtgggaa ggccttttttg      960

```
tgtggctctg gtcttagagt acatcacaaa cttcatactg gtgagaaacc ctatgaatgt   1020
aaggaatgcg ggaaggcctt tagagtgcga caacaactaa cactccatca gagaattcat   1080
actggtgaga acccctatga atgtaaggaa tgtggaaaga cctttagccg tggttatcat   1140
cttattctcc atcacagaat tcatactggt gaaaaacctt acgaatgtaa ggaatgctgg   1200
aaagccttta gtcgctactc acaacttatt tcacatcaga gtattcatat tggtgttaag   1260
ccctatgact gtaaggaatg cgggaaggcc ttcagactac tttcacaact cacacagcat   1320
cagagtattc atattggtga aaaccttat aaatgtaagg aatgtggcaa ggcctttaga   1380
ttgcgccaaa aacttactct acatcagagc attcatactg gcgaaaaacc ctttgagtgt   1440
aaggaatgta ggaaggcctt tagacttaat tcatccctta ttcaacatct gagaattcat   1500
tctggtgaga acccctatga atgtaaggaa tgtaagaagg cctttaggca acattcacac   1560
cttactcatc atctgaaaat tcataatgta aaaatctaa                          1599
```

<210> SEQ ID NO 4
<211> LENGTH: 2635
<212> TYPE: DNA
<213> ORGANISM: Homo sapiens
<220> FEATURE:
<223> OTHER INFORMATION: human zinc finger protein 545 (ZNF545), ZFP82
      zinc finger protein (ZFP82, zpf-82), zinc finger protein 85 cDNA
<220> FEATURE:
<221> NAME/KEY: CDS
<222> LOCATION: (236)...(1834)
<223> OTHER INFORMATION: human zinc finger protein 545 (ZNF545)

<400> SEQUENCE: 4

```
cgttaggccc cggggattgt ggcgtgaccc ggcagcggct tcctccgttc gggcatcgct     60
gtgcctcggg ttcgcgcccc gagtgagcag tcctggcccg gagcgtcggt cctggtaatc    120
tgtaggaaaa gcgctgcggc ccaggggta aagagagatc agcctctgtg gactcggtgc    180
ttctcctggc aagtaaaccc caaggaggac tgaccagttc ttgaatttct atacc atg     238
                                                               Met
                                                                 1 gcc ctt cga tca gtg atg ttc agt gat gta tcc ata gac ttc tct cca     286
Ala Leu Arg Ser Val Met Phe Ser Asp Val Ser Ile Asp Phe Ser Pro
        5                  10                  15 gaa gag tgg gaa tac ctg gac ttg gaa caa aag gac ttg tac aga gat     334
Glu Glu Trp Glu Tyr Leu Asp Leu Glu Gln Lys Asp Leu Tyr Arg Asp
         20                  25                  30 gtc atg ttg gag aac tac agc aac ttg gtc tca ctg gga tgc ttc att     382
Val Met Leu Glu Asn Tyr Ser Asn Leu Val Ser Leu Gly Cys Phe Ile
     35                  40                  45 tct aaa cca gat gtg att tcc tca ttg gag caa gga aaa gag cct tgg     430
Ser Lys Pro Asp Val Ile Ser Ser Leu Glu Gln Gly Lys Glu Pro Trp
 50                  55                  60                  65 aaa gtt gtg agg aaa gga aga aga caa tat cca gat ttg gag acc aag     478
Lys Val Val Arg Lys Gly Arg Arg Gln Tyr Pro Asp Leu Glu Thr Lys
                 70                  75                  80 tat gag acc aag aag tta tct tta gaa aat gac att tat gaa ata aat     526
Tyr Glu Thr Lys Lys Leu Ser Leu Glu Asn Asp Ile Tyr Glu Ile Asn
             85                  90                  95 tta tcc cag tgg aag ata atg gaa aga att gaa aac cat ggc ctt aag     574
Leu Ser Gln Trp Lys Ile Met Glu Arg Ile Glu Asn His Gly Leu Lys
        100                 105                 110 ggt ctc att tta aaa aat gat tgg gaa tcc aca gga aaa att gaa gga     622
Gly Leu Ile Leu Lys Asn Asp Trp Glu Ser Thr Gly Lys Ile Glu Gly
    115                 120                 125
```

-continued

| | | |
|---|---|---|
| cag gag aga cct caa gaa gga tac ttc agt agt gtg aaa atg cca tct<br>Gln Glu Arg Pro Gln Glu Gly Tyr Phe Ser Ser Val Lys Met Pro Ser<br>130                         135                        140                      145 | 670 |
| gaa aag gtg tcc tct tac cag aaa cgc aca tct gtt act cca cat cag<br>Glu Lys Val Ser Ser Tyr Gln Lys Arg Thr Ser Val Thr Pro His Gln<br>                  150                        155                        160 | 718 |
| aga ctt cat ttt gtt gat aaa ccc tat gaa tgt aag gaa tgt ggg aag<br>Arg Leu His Phe Val Asp Lys Pro Tyr Glu Cys Lys Glu Cys Gly Lys<br>                        165                        170                        175 | 766 |
| gcg ttc aga gtg cgc caa cag ctt act ttt cat cac aga att cat act<br>Ala Phe Arg Val Arg Gln Gln Leu Thr Phe His His Arg Ile His Thr<br>        180                        185                        190 | 814 |
| ggt gaa aaa ccg tat gaa tgt aag gaa tgt ggg atg gcc ttc aga cag<br>Gly Glu Lys Pro Tyr Glu Cys Lys Glu Cys Gly Met Ala Phe Arg Gln<br>195                         200                        205 | 862 |
| act gca cac ctt act cga cat cag aga ctt cat tct ggt gaa aaa ctc<br>Thr Ala His Leu Thr Arg His Gln Arg Leu His Ser Gly Glu Lys Leu<br>210                         215                        220                        225 | 910 |
| tat gaa tgt aag gaa tgt ggg gaa gct ttc ata tgt ggt gca gat ctt<br>Tyr Glu Cys Lys Glu Cys Gly Glu Ala Phe Ile Cys Gly Ala Asp Leu<br>                            230                        235                        240 | 958 |
| aga gta cat cag aaa atg cat att ggt gag aag ccc tat gaa tgt aaa<br>Arg Val His Gln Lys Met His Ile Gly Glu Lys Pro Tyr Glu Cys Lys<br>                  245                        250                        255 | 1006 |
| gaa tgt ggg aag gct ttt agg gta cga gga caa ctt act ctg cat cag<br>Glu Cys Gly Lys Ala Phe Arg Val Arg Gly Gln Leu Thr Leu His Gln<br>                        260                        265                        270 | 1054 |
| agg att cat act ggt gag aaa ccc tat gtg tgt aaa gag tgt gga aaa<br>Arg Ile His Thr Gly Glu Lys Pro Tyr Val Cys Lys Glu Cys Gly Lys<br>275                         280                        285 | 1102 |
| gcc ttt aga cag tac gca cac ctg act cgg cat cag aag ctt aat agt<br>Ala Phe Arg Gln Tyr Ala His Leu Thr Arg His Gln Lys Leu Asn Ser<br>290                         295                        300                        305 | 1150 |
| gct gac agg ctc tat gaa tgc aaa gaa tgt ggg aag gcc ttt ttg tgt<br>Ala Asp Arg Leu Tyr Glu Cys Lys Glu Cys Gly Lys Ala Phe Leu Cys<br>                            310                        315                        320 | 1198 |
| ggc tct ggt ctt aga gta cat cac aaa ctt cat act ggt gag aaa ccc<br>Gly Ser Gly Leu Arg Val His His Lys Leu His Thr Gly Glu Lys Pro<br>                  325                        330                        335 | 1246 |
| tat gaa tgt aag gaa tgc ggg aag gcc ttt aga gtg cga caa caa cta<br>Tyr Glu Cys Lys Glu Cys Gly Lys Ala Phe Arg Val Arg Gln Gln Leu<br>                        340                        345                        350 | 1294 |
| aca ctc cat cag aga att cat act ggt gag aaa ccc tat gaa tgt aag<br>Thr Leu His Gln Arg Ile His Thr Gly Glu Lys Pro Tyr Glu Cys Lys<br>355                         360                        365 | 1342 |
| gaa tgt gga aag acc ttt agc cgt ggt tat cat ctt att ctc cat cac<br>Glu Cys Gly Lys Thr Phe Ser Arg Gly Tyr His Leu Ile Leu His His<br>370                         375                        380                        385 | 1390 |
| aga att cat act ggt gaa aaa cct tac gaa tgt aag gaa tgc tgg aaa<br>Arg Ile His Thr Gly Glu Lys Pro Tyr Glu Cys Lys Glu Cys Trp Lys<br>                        390                        395                        400 | 1438 |
| gcc ttt agt cgc tac tca caa ctt att tca cat cag agt att cat att<br>Ala Phe Ser Arg Tyr Ser Gln Leu Ile Ser His Gln Ser Ile His Ile<br>                        405                        410                        415 | 1486 |
| ggt gtt aag ccc tat gac tgt aag gaa tgc ggg aag gcc ttc aga cta<br>Gly Val Lys Pro Tyr Asp Cys Lys Glu Cys Gly Lys Ala Phe Arg Leu<br>        420                        425                        430 | 1534 |
| ctt tca caa ctc aca cag cat cag agt att cat att ggt gag aaa cct<br>Leu Ser Gln Leu Thr Gln His Gln Ser Ile His Ile Gly Glu Lys Pro<br>435                         440                        445 | 1582 |

```
tat aaa tgt aag gaa tgt ggc aag gcc ttt aga ttg cgc caa aaa ctt        1630
Tyr Lys Cys Lys Glu Cys Gly Lys Ala Phe Arg Leu Arg Gln Lys Leu
450                 455                 460                 465 act cta cat cag agc att cat act ggc gaa aaa ccc ttt gag tgt aag        1678
Thr Leu His Gln Ser Ile His Thr Gly Glu Lys Pro Phe Glu Cys Lys
                470                 475                 480 gaa tgt agg aag gcc ttt aga ctt aat tca tcc ctt att caa cat ctg        1726
Glu Cys Arg Lys Ala Phe Arg Leu Asn Ser Ser Leu Ile Gln His Leu
            485                 490                 495 aga att cat tct ggt gag aaa ccc tat gaa tgt aag gaa tgt aag aag        1774
Arg Ile His Ser Gly Glu Lys Pro Tyr Glu Cys Lys Glu Cys Lys Lys
        500                 505                 510 gcc ttt agg caa cat tca cac ctt act cat cat ctg aaa att cat aat        1822
Ala Phe Arg Gln His Ser His Leu Thr His His Leu Lys Ile His Asn
    515                 520                 525 gta aaa atc taa gaaagtcttt tcaacttctg tgttatagaa cattctatga            1874
Val Lys Ile
530 atgtagtaat taatctattt tgctccatac atgcaactgc gttggcatta gaggttttat      1934 accattaaaa gagtgtgaca atgtattgta gtccatcatc actcaaacct gaaacttcag      1994 catatttgtt ctaaaaacta atcctgttat aagaatgaaa aagacattta ccgtcatccc      2054 tatcccatca ctttgtgtca tactggacaa gacgcttaac tgctctgtgc tataattttt     2114 taatttatga catggtcata taagagtgca gcagtttgac acactttcaa tcaagaggtg      2174 gaatctacat ccctctgttg tatacaggaa tctacatccc tctgtgactg cttcgcccag      2234 tagaatatgg tagacgtact gctgtgctgg tttcttgact cagactttac tggtagggtt     2294 acttcatctc atgaaatgac agaactgtct tgttacaaag tctggctact ttgctgaaga     2354 gaccacatga agaggccctg aaactacgta gagagggaga ggcacctgct gaaccctgtc     2414 ttcttgacat ccaccaagat accagacatt tgagtgaaat tttggatcca ccagaccagc     2474 caccagctaa atgccagtga gcgacttggt aacctgaact gatgccatgt agaatggaag     2534 aattgaccag ctgagcccct ggcccaaatt tctgacccac aaaaacatga gatataataa     2594 aatggttgtt gttttaagcc acgaaaaaaa aaaaaaaaa a                          2635
```

<210> SEQ ID NO 5
<211> LENGTH: 532
<212> TYPE: PRT
<213> ORGANISM: Homo sapiens
<220> FEATURE:
<223> OTHER INFORMATION: human zinc finger protein 545 (ZNF545)

<400> SEQUENCE: 5

```
Met Ala Leu Arg Ser Val Met Phe Ser Asp Val Ser Ile Asp Phe Ser
1               5                   10                  15

Pro Glu Glu Trp Glu Tyr Leu Asp Leu Glu Gln Lys Asp Leu Tyr Arg
            20                  25                  30

Asp Val Met Leu Glu Asn Tyr Ser Asn Leu Val Ser Leu Gly Cys Phe
        35                  40                  45

Ile Ser Lys Pro Asp Val Ile Ser Ser Leu Glu Gln Gly Lys Glu Pro
    50                  55                  60

Trp Lys Val Val Arg Lys Gly Arg Arg Gln Tyr Pro Asp Leu Glu Thr
65                  70                  75                  80

Lys Tyr Glu Thr Lys Lys Leu Ser Leu Glu Asn Asp Ile Tyr Glu Ile
                85                  90                  95
```

```
Asn Leu Ser Gln Trp Lys Ile Met Glu Arg Ile Glu Asn His Gly Leu
                100                 105                 110
Lys Gly Leu Ile Leu Lys Asn Asp Trp Glu Ser Thr Gly Lys Ile Glu
            115                 120                 125
Gly Gln Glu Arg Pro Gln Glu Gly Tyr Phe Ser Ser Val Lys Met Pro
        130                 135                 140
Ser Glu Lys Val Ser Ser Tyr Gln Lys Arg Thr Ser Val Thr Pro His
145                 150                 155                 160
Gln Arg Leu His Phe Val Asp Lys Pro Tyr Glu Cys Lys Glu Cys Gly
                165                 170                 175
Lys Ala Phe Arg Val Arg Gln Gln Leu Thr Phe His Gln Arg Ile His
            180                 185                 190
Thr Gly Glu Lys Pro Tyr Glu Cys Lys Glu Cys Gly Met Ala Phe Arg
        195                 200                 205
Gln Thr Ala His Leu Thr Arg His Gln Arg Leu His Ser Gly Glu Lys
    210                 215                 220
Leu Tyr Glu Cys Lys Glu Cys Gly Glu Ala Phe Ile Cys Gly Ala Asp
225                 230                 235                 240
Leu Arg Val His Gln Lys Met His Ile Gly Glu Lys Pro Tyr Glu Cys
                245                 250                 255
Lys Glu Cys Gly Lys Ala Phe Arg Val Arg Gly Gln Leu Thr Leu His
            260                 265                 270
Gln Arg Ile His Thr Gly Glu Lys Pro Tyr Val Cys Lys Glu Cys Gly
        275                 280                 285
Lys Ala Phe Arg Gln Tyr Ala His Leu Thr Arg His Gln Lys Leu Asn
    290                 295                 300
Ser Ala Asp Arg Leu Tyr Glu Cys Lys Glu Cys Gly Lys Ala Phe Leu
305                 310                 315                 320
Cys Gly Ser Gly Leu Arg Val His His Lys Leu His Thr Gly Glu Lys
                325                 330                 335
Pro Tyr Glu Cys Lys Glu Cys Gly Lys Ala Phe Arg Val Arg Gln Gln
            340                 345                 350
Leu Thr Leu His Gln Arg Ile His Thr Gly Glu Lys Pro Tyr Glu Cys
        355                 360                 365
Lys Glu Cys Gly Lys Thr Phe Ser Arg Gly Tyr His Leu Ile Leu His
    370                 375                 380
His Arg Ile His Thr Gly Glu Lys Pro Tyr Glu Cys Lys Glu Cys Trp
385                 390                 395                 400
Lys Ala Phe Ser Arg Tyr Ser Gln Leu Ile Ser His Gln Ser Ile His
                405                 410                 415
Ile Gly Val Lys Pro Tyr Asp Cys Lys Glu Cys Gly Lys Ala Phe Arg
            420                 425                 430
Leu Leu Ser Gln Leu Thr Gln His Gln Ser Ile His Ile Gly Glu Lys
        435                 440                 445
Pro Tyr Lys Cys Lys Glu Cys Gly Lys Ala Phe Arg Leu Arg Gln Lys
    450                 455                 460
Leu Thr Leu His Gln Ser Ile His Thr Gly Glu Lys Pro Phe Glu Cys
465                 470                 475                 480
Lys Glu Cys Arg Lys Ala Phe Arg Leu Asn Ser Ser Leu Ile Gln His
                485                 490                 495
Leu Arg Ile His Ser Gly Glu Lys Pro Tyr Glu Cys Lys Glu Cys Lys
            500                 505                 510
Lys Ala Phe Arg Gln His Ser His Leu Thr His His Leu Lys Ile His
```

Asn Val Lys Ile
    530

<210> SEQ ID NO 6
<211> LENGTH: 20
<212> TYPE: DNA
<213> ORGANISM: Artificial Sequence
<220> FEATURE:
<223> OTHER INFORMATION: synthetic human ZNF545 RT-PCR forward primer
      ZNF545-F

<400> SEQUENCE: 6
gagccttgga aagttgtgag                                              20

<210> SEQ ID NO 7
<211> LENGTH: 21
<212> TYPE: DNA
<213> ORGANISM: Artificial Sequence
<220> FEATURE:
<223> OTHER INFORMATION: synthetic human ZNF545 RT-PCR reverse primer
      ZNF545-R

<400> SEQUENCE: 7
ggcattttca cactactgaa g                                            21

<210> SEQ ID NO 8
<211> LENGTH: 18
<212> TYPE: DNA
<213> ORGANISM: Artificial Sequence
<220> FEATURE:
<223> OTHER INFORMATION: synthetic human beta-actin RT-PCR forward
      primer beta-actin-F

<400> SEQUENCE: 8
gtcttcccct ccatcgtg                                                18

<210> SEQ ID NO 9
<211> LENGTH: 20
<212> TYPE: DNA
<213> ORGANISM: Artificial Sequence
<220> FEATURE:
<223> OTHER INFORMATION: synthetic human beta-actin RT-PCR reverse
      primer beta-actin-R

<400> SEQUENCE: 9
agggtgagga tgcctctctt                                              20

<210> SEQ ID NO 10
<211> LENGTH: 20
<212> TYPE: DNA
<213> ORGANISM: Artificial Sequence
<220> FEATURE:
<223> OTHER INFORMATION: synthetic human heterochromatin protein 1
      (HP1beta) RT-PCR forward primer HP1beta-F

<400> SEQUENCE: 10
tggtaaaggg caaagtggag                                              20

<210> SEQ ID NO 11
<211> LENGTH: 20
<212> TYPE: DNA
<213> ORGANISM: Artificial Sequence
<220> FEATURE:
<223> OTHER INFORMATION: synthetic human heterochromatin protein 1
      (HP1beta) RT-PCR reverse primer HP1beta-R -continued

<400> SEQUENCE: 11
gggcaatcca ggttctcttc                                           20

<210> SEQ ID NO 12
<211> LENGTH: 23
<212> TYPE: DNA
<213> ORGANISM: Artificial Sequence
<220> FEATURE:
<223> OTHER INFORMATION: synthetic human methylated ZNF545 methylation
      specific PCR (MSP) forward primer ZNF545-MSP-MF

<400> SEQUENCE: 12
ttttttttag gttttgtcgc gtc                                       23

<210> SEQ ID NO 13
<211> LENGTH: 21
<212> TYPE: DNA
<213> ORGANISM: Artificial Sequence
<220> FEATURE:
<223> OTHER INFORMATION: synthetic human methylated ZNF545 methylation
      specific PCR (MSP) reverse primer ZNF545-MSP-MR

<400> SEQUENCE: 13
ctactaaaaa aaccgaacgc g                                         21

<210> SEQ ID NO 14
<211> LENGTH: 24
<212> TYPE: DNA
<213> ORGANISM: Artificial Sequence
<220> FEATURE:
<223> OTHER INFORMATION: synthetic human unmethylated ZNF545 methylation
      specific PCR (MSP) forward primer ZNF545-MSP-UF

<400> SEQUENCE: 14 tttttttta ggttttgttg tgtt                                       24

<210> SEQ ID NO 15
<211> LENGTH: 22
<212> TYPE: DNA
<213> ORGANISM: Artificial Sequence
<220> FEATURE:
<223> OTHER INFORMATION: synthetic human unmethylated ZNF545 methylation
      specific PCR (MSP) reverse primer ZNF545-MSP-UR

<400> SEQUENCE: 15
ccaaacacac tcacaaaata ca                                        22

<210> SEQ ID NO 16
<211> LENGTH: 23
<212> TYPE: DNA
<213> ORGANISM: Artificial Sequence
<220> FEATURE:
<223> OTHER INFORMATION: synthetic human ZNF545 bisulfite genomic
      sequencing (BGS) forward primer ZNF545-BGS-F

<400> SEQUENCE: 16
gtatagggtt ttttagttgg tat                                       23

<210> SEQ ID NO 17
<211> LENGTH: 20
<212> TYPE: DNA
<213> ORGANISM: Artificial Sequence
<220> FEATURE:
<223> OTHER INFORMATION: synthetic human ZNF545 bisulfite genomic
      sequencing (BGS) reverse primer ZNF545-BGS-R

```
<400> SEQUENCE: 17
cctctctctt tacccccta                                                  20

<210> SEQ ID NO 18
<211> LENGTH: 21
<212> TYPE: DNA
<213> ORGANISM: Artificial Sequence
<220> FEATURE:
<223> OTHER INFORMATION: synthetic human ZNF545 small interfering RNA
      (siRNA) sense strand
<220> FEATURE:
<223> OTHER INFORMATION: Description of Combined DNA/RNA Molecule:
      synthetic human ZNF545 small interfering RNA (siRNA) sense strand

<400> SEQUENCE: 18
ccgugguuau caucuuauut t                                               21

<210> SEQ ID NO 19
<211> LENGTH: 21
<212> TYPE: DNA
<213> ORGANISM: Artificial Sequence
<220> FEATURE:
<223> OTHER INFORMATION: synthetic human ZNF545 small interfering RNA
      (siRNA) antisense strand
<220> FEATURE:
<223> OTHER INFORMATION: Description of Combined DNA/RNA Molecule:
      synthetic human ZNF545 small interfering RNA (siRNA) antisense
      strand

<400> SEQUENCE: 19
ttggcaccaa uaguagaaua a                                               21

<210> SEQ ID NO 20
<211> LENGTH: 20
<212> TYPE: DNA
<213> ORGANISM: Artificial Sequence
<220> FEATURE:
<223> OTHER INFORMATION: synthetic human ribosomal DNA (rDNA) PCR
      forward primer

<400> SEQUENCE: 20
cccgggggag gtatatcttt                                                 20

<210> SEQ ID NO 21
<211> LENGTH: 20
<212> TYPE: DNA
<213> ORGANISM: Artificial Sequence
<220> FEATURE:
<223> OTHER INFORMATION: synthetic human ribosomal DNA (rDNA) PCR
      reverse primer

<400> SEQUENCE: 21
gacgtcacca catcgatcac                                                 20

<210> SEQ ID NO 22
<211> LENGTH: 21
<212> TYPE: DNA
<213> ORGANISM: Artificial Sequence
<220> FEATURE:
<223> OTHER INFORMATION: synthetic human heterochromatin protein 1
      (HP1beta) small interfering RNA (siRNA) sense strand
<220> FEATURE:
<223> OTHER INFORMATION: Description of Combined DNA/RNA Molecule:
      synthetic human heterochromatin protein 1 (HP1beta) small
      interfering RNA (siRNA) sense strand

<400> SEQUENCE: 22
ggaagggauu cucagaugat t                                               21
```

```
<210> SEQ ID NO 23
<211> LENGTH: 21
<212> TYPE: DNA
<213> ORGANISM: Artificial Sequence
<220> FEATURE:
<223> OTHER INFORMATION: synthetic human heterochromatin protein 1
      (HP1beta) small interfering RNA (siRNA) antisense strand
<220> FEATURE:
<223> OTHER INFORMATION: Description of Combined DNA/RNA Molecule:
      synthetic human heterochromatin protein 1 (HP1beta) small
      interfering RNA (siRNA) antisense strand

<400> SEQUENCE: 23
ttccuucccu aagagucuac u                                              21

<210> SEQ ID NO 24
<211> LENGTH: 20
<212> TYPE: DNA
<213> ORGANISM: Artificial Sequence
<220> FEATURE:
<223> OTHER INFORMATION: synthetic human ribosomal DNA (rDNA) chromatin
      immunoprecipitation PCR (ChIP-PCR) forward primer

<400> SEQUENCE: 24
cccgggggag gtatatcttt                                                20

<210> SEQ ID NO 25
<211> LENGTH: 18
<212> TYPE: DNA
<213> ORGANISM: Artificial Sequence
<220> FEATURE:
<223> OTHER INFORMATION: synthetic human ribosomal DNA (rDNA) chromatin
      immunoprecipitation PCR (ChIP-PCR) reverse primer

<400> SEQUENCE: 25
ccaacctctc cgacgaca                                                  18
```

EPIGENETIC BIOMARKER ZNF545 FOR DIAGNOSING AND PROGNOSIS OF GASTRIC CANCER

REFERENCE TO A "SEQUENCE LISTING," A TABLE, OR A COMPUTER PROGRAM LISTING APPENDIX SUBMITTED AS AN ASCII TEXT FILE

The Sequence Listing written in file -133.TXT, created on May 8, 2013, 24,576 bytes, machine format IBM-PC, MS-Windows operating system, is hereby incorporated by reference in its entirety for all purposes.

BACKGROUND OF THE INVENTION

Gastric cancer, also known as stomach cancer, is the fourth most common cancer worldwide with approximately 1,000,000 cases diagnosed annually. It is a disease with a high mortality rate (about 800,000 deaths per year), making it the second most common cause of cancer death worldwide after lung cancer. The incidence of gastric cancer is significantly higher among men and in developing nations, including many Asian countries.

Gastric cancer often remains asymptomatic or exhibits only nonspecific symptoms in its early stages, diagnosis in many cases is therefore not made until the disease has reached an advanced stage. This leads to a generally poor prognosis: metastasis occurs in 80-90% of individuals diagnosed with gastric cancer, with a six-month survival rate of 65% in those diagnosed in early stages and less than 15% of those diagnosed in late stages.

Because of the prevalence of gastric cancer and its grave implications on patients' life expectancy, there exists a need for new methods to diagnose, monitor, and treat gastric cancer. This invention fulfills this and other related needs.

BRIEF SUMMARY OF THE INVENTION

In a first aspect, the present invention provides a method for detecting gastric cancer in a subject. The method includes the steps of: (a) measuring expression level of ZNF545 in a sample taken from the subject, and (b) comparing the expression level obtained in step (a) with a standard control. When a decrease in the expression level of ZNF545 is detected as compared with the standard control, it indicates that the subject may have gastric cancer. Typically, the sample used in the method is a stomach mucosa sample, e.g., one that includes stomach epithelial cells.

In some embodiments, the expression level of ZNF545 is the ZNF545 protein level. In other embodiments, the expression level of ZNF545 is ZNF545 mRNA level. When the ZNF545 protein level is measured, step (a) may include an immunoassay using an antibody that specifically binds the ZNF545 protein. For example, a Western Blot analysis may be used. In other cases, step (a) may involve mass spectrometry, or a hybridization-based assay such as hybridization to a microarray, fluorescence probe, or molecular beacon.

When ZNF545 mRNA level is measured, step (a) in some cases may involve an amplification reaction, such as a polymerase chain reaction (PCR), especially a reverse transcriptase-PCR (RT-PCR). In other cases, the detecting step may involve a polynucleotide hybridization assay, such as a Southern Blot analysis or Northern Blot analysis or an in situ hybridization assay. For example, a polynucleotide probe may be used in the polynucleotide hybridization assay to hybridize with SEQ ID NO:3 or 4 or a complement thereof. In some cases, the polynucleotide probe may include a detectable moiety.

In some embodiments, when the subject is indicated as having gastric cancer after the first round of method steps described above, the claimed method may further include repeating step (a) at a later time using the same type of sample from the subject. An increase in the expression level of ZNF545 at the later time as compared to the amount from the original step (a) indicates an improvement of gastric cancer, whereas a decrease indicates a worsening of gastric cancer.

In a second aspect, the present invention provides another method for detecting gastric cancer in a subject. The method includes the steps of: (a) treating a sample taken from the subject with an agent that differentially modifies methylated and unmethylated DNA; and (b) determining whether each CpG in a CpG-containing genomic sequence is methylated or unmethylated, with the CpG-containing genomic sequence being at least a segment of SEQ ID NO:1 or 2 and comprising at least one CpG. When the presence of one methylated CpG is detected in the CpG-containing genomic sequence, it indicates that the subject may have gastric cancer.

In some embodiments, the CpG-containing genomic sequence contains two or more CpG, and when at least 50% of all CpG being methylated the subject is indicated as having gastric cancer. In some cases, the CpG-containing genomic sequence is a segment of at least 15, 20, 50, or more contiguous nucleotides of SEQ ID NO:1 or 2. In other cases, the CpG-containing genomic sequence is SEQ ID NO:1 or 2. In one embodiment of the claimed method, the CpG-containing genomic sequence is SEQ ID NO:1, and when at least 5 of all CpG in the CpG-containing genomic sequence are methylated, the subject is indicated as likely having gastric cancer. In one embodiment of the claimed method, the CpG-containing genomic sequence is SEQ ID NO:1, and when at least 19 of all CpG in the CpG-containing genomic sequence are methylated, the subject is indicated as likely having gastric cancer.

In some examples, the sample used in the claimed method is a gastric tissue sample. In other examples, the sample used in the claimed method is a stomach mucosa sample.

In some examples, when the subject is indicated as having gastric cancer after the first round of method steps described above, the method further involves repeating steps (a) and (b) at a later time using the sample type of sample from the subject. When an increase is detected in the number of methylated CpG at the later time as compared to the number of methylated CpG determined from the original step (b), it indicates a worsening of gastric cancer, whereas a decrease indicates an improvement of gastric cancer.

In other examples, when the subject is indicated as having gastric cancer after the first round of method steps described above, the method further involves repeating steps (a) and (b) using a non-cancer sample adjacent to the sample of the original step (a) from the subject. The presence of methylated CpG in the non-cancer sample indicates an increased likelihood of a shortened survival for the subject.

In some embodiments, the agent used in the claimed method to differentially modify methylated DNA and unmethylated DNA is an enzyme that preferentially cleaves methylated DNA, an enzyme that preferentially cleaves unmethylated DNA, or a bisulfite. In other embodiments, step (b) of the method involves an amplification reaction; or step (b) may involve sequencing of a DNA molecule.

In some embodiments, the amplification reaction is a polymerase chain reaction. In some cases the PCR reaction comprises a pair of oligonucleotide primers having the nucleotide sequence set forth in SEQ ID NOs: 16 and 17. In some embodiments, the amplification reaction is followed by DNA sequencing. In some embodiments, the amplification reaction is a methylation-specific polymerase chain reaction (MSP). In some cases the MSP reaction comprises a pair of oligonucleotide primers having the nucleotide sequence set forth in SEQ ID NOs: 12 and 13 and/or a pair of oligonucleotide primers having the nucleotide sequence set forth in SEQ ID NOs: 14 and 15.

In some embodiments, the method further comprises performing a diagnostic assay to the subject identified as having an increase in the expression level of ZNF545. Non-limiting examples of a diagnostic assay include an imaging test, such as, computerized tomography (CT), positron emission tomography (PET), magnetic resonance imaging (MRI), or exploratory surgery, such as, laparoscopy. In some embodiments, the method further comprises administering a therapy directed to ameliorating gastric cancer to the subject identified as having an increase in the expression level of ZNF545. Non-limiting examples of a therapy for ameliorating gastric cancer include surgery, e.g., endoscopic mucosal resection, subtotal gastrectomy, and total gastrectomy, radiation therapy, chemotherapy, administration of targeted therapy drugs, e.g., trastuzumab (Herceptin), or a combination thereof. As described herein, an increase in the expression level of ZNF545 includes an increase in ZNF545 RNA level of ZNF545 protein level compared to a standard control, or the presence of at least one methylated CpG in the CpG-containing genomic sequence.

In a third aspect, the present invention provides a kit for detecting gastric cancer in a subject, comprising (1) a standard control that provides an average amount of ZNF545 protein or ZNF545 mRNA; and (2) an agent that specifically and quantitatively identifies ZNF545 protein or ZNF545 mRNA. In some cases, the agent may be an antibody that specifically binds the ZNF545 protein (SEQ ID NO: 5) or a portion thereof; or the agent may be a polynucleotide probe that hybridizes with the ZNF545 mRNA (SEQ ID NO:4). For example, the polynucleotide probe binds to the nucleotide sequence set forth in SEQ ID NO:3 or 4 or a complement thereof. The agent may include a detectable moiety. In other cases, the kit may further comprise two oligonucleotide primers for specifically amplifying at least a segment of SEQ ID NO:3 or 4 or its complement in an amplification reaction. In some instances, the two oligonucleotide primers comprise the nucleotide sequence set forth in SEQ ID NOs:6 and 7. Typically, the kit will further include an instruction manual.

In a fourth aspect, the present invention provides a method for inhibiting growth of a gastric cancer cell. The claimed method includes the step of contacting the gastric cancer cell with (1) an effective amount of a polypeptide that comprises the amino acid sequence set forth in SEQ ID NO:5 or (2) a nucleic acid that comprises a polynucleotide sequence encoding SEQ ID NO:5. In some embodiments, the nucleic acid is an expression cassette comprising a promoter operably linked to the polynucleotide sequence encoding SEQ ID NO:5. In other embodiments, the nucleic acid comprises the polynucleotide sequence set forth in SEQ ID NO:3 or 4. Various promoters may be useful in this method, for example, the promoter may be an epithelium-specific promoter. In yet other embodiments, the gastric cancer cell is within a patient's body.

In a fifth aspect, the present invention provides an isolated nucleic acid having the nucleotide sequence at least 95% identical to a segment of about 20-100 contiguous nucleotides of SEQ ID NO:1-4, 6, 7, 12-16, or 17 or complement thereof. In some embodiments, the nucleic acid has the nucleotide sequence identical to a segment of about 20-100 contiguous nucleotides of SEQ ID NO: 1-4, 6, 7, 12-16, or 17 or complement thereof. In other embodiments, the nucleic acid is conjugated to a detectable moiety.

In addition, the present invention provides a kit for detecting gastric cancer. The kit comprises: (1) an agent that differentially modifies methylated and unmethylated DNA, and (2) an indicator that, after the agent has been used to treat a sample from a subject who is being tested for gastric cancer, determines whether each CpG in a CpG-containing genomic sequence is methylated or unmethylated. The CpG-containing genomic sequence is at least a segment of SEQ ID NO:1 or 2 and comprises at least one CpG. The present invention also provides a composition for inhibiting growth of a gastric cancer cell. The composition contains an effective amount of (1) a polypeptide comprising the amino acid sequence set forth in SEQ ID NO:5 (e.g., a polypeptide consisting of the amino acid sequence of SEQ ID NO:5) or (2) a nucleic acid comprising or consisting of a polynucleotide sequence encoding SEQ ID NO:5 (e.g., a nucleic acid sequence comprising the polynucleotide sequence of SEQ ID NO:2 or 3), and a pharmaceutically acceptable carrier. In this regard, this invention further provides the use of a polypeptide comprising the amino acid sequence set forth in SEQ ID NO:5 (e.g., a polypeptide consisting of the amino acid sequence of SEQ ID NO:5) or a nucleic acid comprising a polynucleotide sequence encoding SEQ ID NO:2 or 3 (e.g., a nucleic acid sequence comprising or consisting of the polynucleotide sequence of SEQ ID NO:2 or 3) in preparing a medicament for inhibiting growth of a gastric cancer cell. Moreover, the present invention provides a use of a polynucleotide sequence that comprises or consists of a segment of SEQ ID NO:1, 2, 3, or 4 or complement thereof in preparing a kit for detecting gastric cancer. The segment is typically about 20-100 contiguous nucleotides of SEQ ID NO:1, 2, 3, or 4 or its complement.

BRIEF DESCRIPTION OF THE DRAWINGS

FIG. 6. Univariate Cox regression analysis of potential prognostic factor for patients with gastric cancer. The table illustrates that ZNF545 methylation in adjacent non-tumour tissues, wherein their corresponding tumour tissues are also methylated, is associated with a significantly increased risk of cancer-related death.

FIG. 7. Multivariate Cox regression analysis of potential prognostic factor for patients with gastric cancer. The table illustrates that after adjustments for agent and gender and TNM stage, ZNF545 methylation in adjacent non-tumour tissues is a predictor of poorer survival.

FIG. 8. The table shows a list of primer sequences described herein.

FIG. 9. The figure shows clinicopathologic features of ZNF545 methylation in cancer tissues of gastric cancer patients.

FIG. 10. The figure shows clinicopathologic features of ZNF545 methylation in adjacent non-tumour tissues of gastric cancer patients.

DETAILED DESCRIPTION OF THE INVENTION

Figure 1:
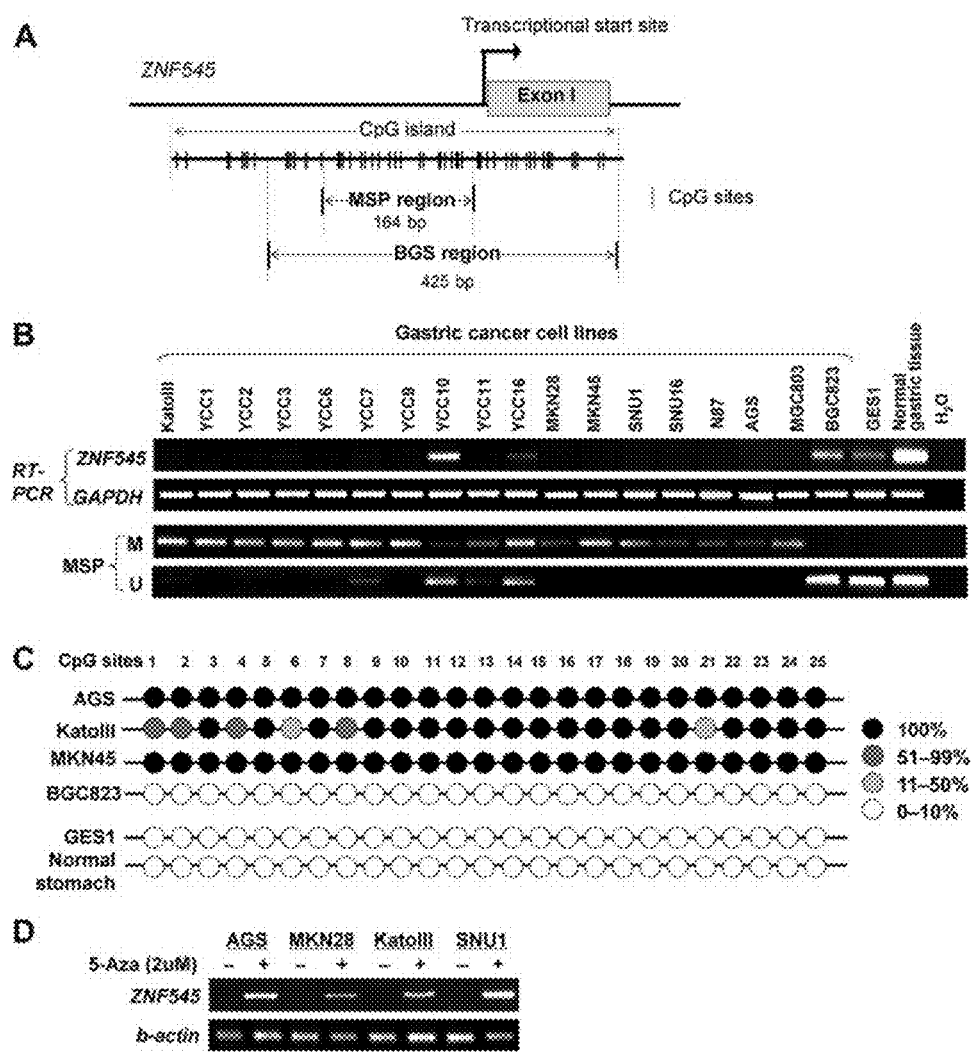
FIG. 1. ZNF545 is inactivated by promoter methylation in gastric cancer. (A) The CpG island of ZNF545. The transcriptional start site and methylation-specific PCR (MSP) and bisulfite genomic sequencing (BGS) regions are indicated. (B) Silencing of ZNF545 in gastric cancer cell lines by promoter methylation. Methylation of ZNF545 was determined by MSP. M denotes methylated; U denotes unmethylated. Normal gastric tissue was epithelial tissue, mainly comprising epithelial cells. (C) Methylation status of the ZNF545 promoter confirmed by BGS. (D) Pharmacological demethylation with 5-Aza restored ZNF545 expression.

The term "ZNF545 gene" or "ZNF545 protein," as used herein, refers to any naturally occurring variants or mutants, interspecies homologs or orthologs, or man-made variants of human ZNF545 gene or ZNF545 protein. The human ZNF545 gene is located on chromosome 19q13.12. The cDNA sequence of a human wild-type ZNF545 gene is set forth in GenBank Accession No. NM_133466.2 (provided herein as SEQ ID NO:4), encoding a 532-amino acid ZNF545 protein (provided herein as SEQ ID NO:5). A ZNF545 protein within the meaning of this application typically has at least 80%, or 90%, or 95% or higher sequence identity to the human wild-type ZNF545 protein.

In this disclosure the terms "gastric cancer" and "stomach cancer" have the same meaning and refer to a cancer of the stomach or of stomach cells. Such cancers may be adenocarcinomas that occur in the lining of the stomach (mucosa or stomach epithelium) and may be in pylorus, body, or cardial (lower, body and upper) parts of the stomach. A "gastric cancer cell" is a stomach epithelial cell possessing characteristics of gastric cancer and encompasses a precancerous cell, which is in the early stages of conversion to a cancer cell or which is predisposed for conversion to a cancer cell. Such cells may exhibit one or more phenotypic traits characteristic of the cancerous cells.

In this disclosure the term "or" is generally employed in its sense including "and/or" unless the content clearly dictates otherwise.

As used herein, the term "gene expression" is used to refer to the transcription of a DNA to form an RNA molecule encoding a particular protein (e.g., human ZNF545 protein) or the translation of a protein encoded by a polynucleotide sequence. In other words, both mRNA level and protein level encoded by a gene of interest (e.g., human ZNF545gene) are encompassed by the term "gene expression level" in this disclosure.

In this disclosure the term "biological sample" or "sample" includes sections of tissues such as biopsy and autopsy samples, and frozen sections taken for histologic purposes, or processed forms of any of such samples. Biological samples include blood and blood fractions or products (e.g., serum, plasma, platelets, red blood cells, and the like), sputum or saliva, lymph and tongue tissue, cultured cells, e.g., primary cultures, explants, and transformed cells, stool, urine, stomach biopsy tissue etc. A biological sample is typically obtained from a eukaryotic organism, which may be a mammal, may be a primate and may be a human subject.

In this disclosure the term "biopsy" refers to the process of removing a tissue sample for diagnostic or prognostic evaluation, and to the tissue specimen itself. Any biopsy technique known in the art can be applied to the diagnostic and prognostic methods of the present invention. The biopsy technique applied will depend on the tissue type to be evaluated (e.g., tongue, colon, prostate, kidney, bladder, lymph node, liver, bone marrow, blood cell, stomach tissue, etc.) among other factors. Representative biopsy techniques include, but are not limited to, excisional biopsy, incisional biopsy, needle biopsy, surgical biopsy, and bone marrow biopsy and may comprise colonoscopy. A wide range of biopsy techniques are well known to those skilled in the art who will choose between them and implement them with minimal experimentation.

In this disclosure the term "isolated" nucleic acid molecule means a nucleic acid molecule that is separated from other nucleic acid molecules that are usually associated with the isolated nucleic acid molecule. Thus, an "isolated" nucleic acid molecule includes, without limitation, a nucleic acid molecule that is free of nucleotide sequences that naturally flank one or both ends of the nucleic acid in the genome of the organism from which the isolated nucleic acid is derived (e.g., a cDNA or genomic DNA fragment produced by PCR or restriction endonuclease digestion). Such an isolated nucleic acid molecule is generally introduced into a vector (e.g., a cloning vector or an expression vector) for convenience of manipulation or to generate a fusion nucleic acid molecule. In addition, an isolated nucleic acid molecule can include an engineered nucleic acid molecule such as a recombinant or a synthetic nucleic acid molecule. A nucleic acid molecule existing among hundreds to millions of other nucleic acid molecules within, for example, a nucleic acid library (e.g., a cDNA or genomic library) or a gel (e.g., agarose, or polyacrylamine) containing restriction-digested genomic DNA, is not an "isolated" nucleic acid.

The term "nucleic acid" or "polynucleotide" refers to deoxyribonucleic acids (DNA) or ribonucleic acids (RNA) and polymers thereof in either single- or double-stranded form. Unless specifically limited, the term encompasses nucleic acids containing known analogs of natural nucleotides that have similar binding properties as the reference nucleic acid and are metabolized in a manner similar to naturally occurring nucleotides. Unless otherwise indicated, a particular nucleic acid sequence also implicitly encompasses conservatively modified variants thereof (e.g., degenerate codon substitutions), alleles, orthologs, single nucleotide polymorphisms (SNPs), and complementary sequences as well as the sequence explicitly indicated. Specifically, degenerate codon substitutions may be achieved by generating sequences in which the third position of one or more selected (or all) codons is substituted with mixed-base and/or deoxyinosine residues (Batzer et al., *Nucleic Acid Res.* 19:5081 (1991); Ohtsuka et al., *J. Biol. Chem.* 260:2605-2608 (1985); and Rossolini et al., *Mol. Cell. Probes* 8:91-98 (1994)). The term nucleic acid is used interchangeably with gene, cDNA, and mRNA encoded by a gene.

The term "gene" means the segment of DNA involved in producing a polypeptide chain; it includes regions preceding and following the coding region (leader and trailer) involved in the transcription/translation of the gene product and the regulation of the transcription/translation, as well as intervening sequences (introns) between individual coding segments (exons).

In this application, the terms "polypeptide," "peptide," and "protein" are used interchangeably herein to refer to a polymer of amino acid residues. The terms apply to amino acid polymers in which one or more amino acid residue is an artificial chemical mimetic of a corresponding naturally occurring amino acid, as well as to naturally occurring amino acid polymers and non-naturally occurring amino acid polymers. As used herein, the terms encompass amino acid chains of any length, including full-length proteins (i.e., antigens), wherein the amino acid residues are linked by covalent peptide bonds.

The term "amino acid" refers to refers to naturally occurring and synthetic amino acids, as well as amino acid analogs and amino acid mimetics that function in a manner similar to the naturally occurring amino acids. Naturally occurring amino acids are those encoded by the genetic code, as well as those amino acids that are later modified, e.g., hydroxyproline, γ-carboxyglutamate, and O-phosphoserine. For the purposes of this application, amino acid analogs refers to compounds that have the same basic chemical structure as a naturally occurring amino acid, i.e., an a carbon that is bound to a hydrogen, a carboxyl group, an amino group, and an R group, e.g., homoserine, norleucine, methionine sulfoxide, methionine methyl sulfonium. Such analogs have modified R groups (e.g., norleucine) or modified peptide backbones, but retain the same basic chemical structure as a naturally occurring amino acid. For the purposes of this application, amino acid mimetics refers to chemical compounds that have a structure that is different from the general chemical structure of an amino acid, but that functions in a manner similar to a naturally occurring amino acid.

Amino acids may include those having non-naturally occurring D-chirality, as disclosed in WO01/12654, which may improve the stability (e.g., half life), bioavailability, and other characteristics of a polypeptide comprising one or more of such D-amino acids. In some cases, one or more, and potentially all of the amino acids of a therapeutic polypeptide have D-chirality.

Amino acids may be referred to herein by either the commonly known three letter symbols or by the one-letter symbols recommended by the IUPAC-IUB Biochemical Nomenclature Commission. Nucleotides, likewise, may be referred to by their commonly accepted single-letter codes.

As used in herein, the terms "identical" or percent "identity," in the context of describing two or more polynucleotide or amino acid sequences, refer to two or more sequences or subsequences that are the same or have a specified percentage of amino acid residues or nucleotides that are the same (for example, a variant ZNF545 protein used in the method of this invention (e.g., for treating gastric cancer) has at least 80% sequence identity, preferably 85%, 90%, 91%, 92%, 93, 94%, 95%, 96%, 97%, 98%, 99%, or 100% identity, to a reference sequence, e.g., a wild-type human ZNF545 protein), when compared and aligned for maximum correspondence over a comparison window, or designated region as measured using one of the following sequence comparison algorithms or by manual alignment and visual inspection. Such sequences are then said to be "substantially identical." With regard to polynucleotide sequences, this definition also refers to the complement of a test sequence. Preferably, the identity exists over a region that is at least about 50 amino acids or nucleotides in length, or more preferably over a region that is 75-100 amino acids or nucleotides in length.

For sequence comparison, typically one sequence acts as a reference sequence, to which test sequences are compared. When using a sequence comparison algorithm, test and reference sequences are entered into a computer, subsequence coordinates are designated, if necessary, and sequence algorithm program parameters are designated. Default program parameters can be used, or alternative parameters can be designated. The sequence comparison algorithm then calculates the percent sequence identities for the test sequences relative to the reference sequence, based on the program parameters. For sequence comparison of nucleic acids and proteins, the BLAST and BLAST 2.0 algorithms and the default parameters discussed below are used.

A "comparison window", as used herein, includes reference to a segment of any one of the number of contiguous positions selected from the group consisting of from 20 to 600, usually about 50 to about 200, more usually about 100 to about 150 in which a sequence may be compared to a reference sequence of the same number of contiguous positions after the two sequences are optimally aligned. Methods of alignment of sequences for comparison are well-known in the art. Optimal alignment of sequences for comparison can be conducted, e.g., by the local homology algorithm of Smith & Waterman, *Adv. Appl. Math.* 2:482 (1981), by the homology alignment algorithm of Needleman & Wunsch, *J. Mol. Biol.* 48:443 (1970), by the search for similarity method of Pearson & Lipman, *Proc. Nat'l. Acad. Sci. USA* 85:2444 (1988), by computerized implementations of these algorithms (GAP, BESTFIT, FASTA, and TFASTA in the Wisconsin Genetics Software Package, Genetics Computer Group, 575 Science Dr., Madison, Wis.), or by manual alignment and visual inspection (see, e.g., *Current Protocols in Molecular Biology* (Ausubel et al., eds. 1995 supplement)).

Examples of algorithms that are suitable for determining percent sequence identity and sequence similarity are the BLAST and BLAST 2.0 algorithms, which are described in Altschul et al., (1990) *J. Mol. Biol.* 215: 403-410 and Altschul et al. (1977) *Nucleic Acids Res.* 25: 3389-3402, respectively. Software for performing BLAST analyses is publicly available at the National Center for Biotechnology Information website, ncbi.nlm.nih.gov. The algorithm involves first identifying high scoring sequence pairs (HSPs) by identifying short words of length W in the query sequence, which either match or satisfy some positive-valued threshold score T when aligned with a word of the same length in a database sequence. T is referred to as the neighborhood word score threshold (Altschul et al., supra). These initial neighborhood word hits acts as seeds for initiating searches to find longer HSPs containing them. The word hits are then extended in both directions along each sequence for as far as the cumulative alignment score can be increased. Cumulative scores are calculated using, for nucleotide sequences, the parameters M (reward score for a pair of matching residues; always >0) and N (penalty score for mismatching residues; always <0). For amino acid sequences, a scoring matrix is used to calculate the cumulative score. Extension of the word hits in each direction are halted when: the cumulative alignment score falls off by the quantity X from its maximum achieved value; the cumulative score goes to zero or below, due to the accumulation of one or more negative-scoring residue alignments; or the end of either sequence is reached. The BLAST algorithm parameters W, T, and X determine the sensitivity and speed of the alignment. The BLASTN program (for nucleotide sequences) uses as defaults a word size (W) of 28, an expectation (E) of 10, M=1, N=−2, and a comparison of both strands. For amino acid sequences, the BLASTP program uses as defaults a word size (W) of 3, an expectation (E) of 10, and the BLOSUM62 scoring matrix (see Henikoff and Henikoff, *Proc. Natl. Acad. Sci. USA* 89:10915 (1989)).

The BLAST algorithm also performs a statistical analysis of the similarity between two sequences (see, e.g., Karlin and Altschul, *Proc. Nat'l. Acad. Sci. USA* 90:5873-5787 (1993)). One measure of similarity provided by the BLAST algorithm is the smallest sum probability (P(N)), which provides an indication of the probability by which a match between two nucleotide or amino acid sequences would occur by chance. For example, a nucleic acid is considered similar to a reference sequence if the smallest sum probability in a comparison of the test nucleic acid to the reference nucleic acid is less than about 0.2, more preferably less than about 0.01, and most preferably less than about 0.001.

An indication that two nucleic acid sequences or polypeptides are substantially identical is that the polypeptide encoded by the first nucleic acid is immunologically cross reactive with the antibodies raised against the polypeptide encoded by the second nucleic acid, as described below. Thus, a polypeptide is typically substantially identical to a second polypeptide, for example, where the two peptides differ only by conservative substitutions. Another indication that two nucleic acid sequences are substantially identical is that the two molecules or their complements hybridize to each other under stringent conditions, as described below. Yet another indication that two nucleic acid sequences are substantially identical is that the same primers can be used to amplify the sequence.

In this disclosure the terms "stringent hybridization conditions" and "high stringency" refer to conditions under which a probe will hybridize to its target subsequence, typically in a complex mixture of nucleic acids, but to no other sequences. Stringent conditions are sequence-dependent and will be different in different circumstances. Longer sequences hybridize specifically at higher temperatures. An extensive guide to the hybridization of nucleic acids is found in Tijssen, Techniques in Biochemistry and Molecular Biology—Hybridization with Nucleic Probes, "Overview of principles of hybridization and the strategy of nucleic acid assays" (1993) and will be readily understood by those skilled in the art. Generally, stringent conditions are selected to be about 5-10° C. lower than the thermal melting point ($T_m$) for the specific sequence at a defined ionic strength pH. The $T_m$ is the temperature (under defined ionic strength, pH, and nucleic concentration) at which 50% of the probes complementary to the target hybridize to the target sequence at equilibrium (as the target sequences are present in excess, at $T_m$, 50% of the probes are occupied at equilibrium). Stringent conditions may also be achieved with the addition of destabilizing agents such as formamide. For selective or specific hybridization, a positive signal is at least two times background, preferably 10 times background hybridization. Exemplary stringent hybridization conditions can be as following: 50% formamide, 5×SSC, and 1% SDS, incubating at 42° C., or, 5×SSC, 1% SDS, incubating at 65° C., with wash in 0.2×SSC, and 0.1% SDS at 65° C.

Nucleic acids that do not hybridize to each other under stringent conditions are still substantially identical if the polypeptides which they encode are substantially identical. This occurs, for example, when a copy of a nucleic acid is created using the maximum codon degeneracy permitted by the genetic code. In such cases, the nucleic acids typically hybridize under moderately stringent hybridization conditions. Exemplary "moderately stringent hybridization conditions" include a hybridization in a buffer of 40% formamide, 1 M NaCl, 1% SDS at 37° C., and a wash in 1×SSC at 45° C. A positive hybridization is at least twice background. Those of ordinary skill will readily recognize that alternative hybridization and wash conditions can be utilized to provide conditions of similar stringency. Additional guidelines for determining hybridization parameters are provided in numerous references, e.g., Current Protocols in Molecular Biology, ed. Ausubel, et al.

An "expression cassette" is a nucleic acid construct, generated recombinantly or synthetically, with a series of specified nucleic acid elements that permit transcription of a particular polynucleotide sequence in a host cell. An expression cassette may be part of a plasmid, viral genome, or nucleic acid fragment. Typically, an expression cassette includes a polynucleotide to be transcribed, operably linked to a promoter. "Operably linked" in this context means two or more genetic elements, such as a polynucleotide coding sequence and a promoter, placed in relative positions that permit the proper biological functioning of the elements, such as the promoter directing transcription of the coding sequence. Other elements that may be present in an expression cassette include those that enhance transcription (e.g., enhancers) and terminate transcription (e.g., terminators), as well as those that confer certain binding affinity or antigenicity to the recombinant protein produced from the expression cassette.

The term "bisulfite" as used herein encompasses all types of bisulfites, such as sodium bisulfite, that are capable of chemically converting a cytosine (C) to a uracil (U) without chemically modifying a methylated cytosine and therefore can be used to differentially modify a DNA sequence based on the methylation status of the DNA.

As used herein, a reagent that "differentially modifies" methylated or non-methylated DNA encompasses any reagent that reacts differentially with methylated and unmethylated DNA in a process through which distinguishable products or quantitatively distinguishable results (e.g. degree of binding or precipitation) are generated from methylated and non-methylated DNA, thereby allowing the identification of the DNA methylation status. Such processes may include, but are not limited to, chemical reactions (such as an unmethylated C→U conversion by bisulfite), enzymatic treatment (such as cleavage by a methylation-dependent endonuclease), binding, and precipitation. Thus, an enzyme that preferentially cleaves methylated DNA is one capable of cleaving a DNA molecule at a much higher efficiency when the DNA is methylated, whereas an enzyme that preferentially cleaves unmethylated DNA exhibits a significantly higher efficiency when the DNA is not methylated. In the context of the present invention, a reagent that "differentially modifies" methylated and unmethylated DNA also refers to any reagent that exhibits differential ability in its binding to DNA sequences or precipitation of DNA sequences depending on their methylation status. One class of such reagents consists of methylated DNA binding proteins.

A "CpG-containing genomic sequence" as used herein refers to a segment of DNA sequence at a defined location in the genome of an individual. Typically, a "CpG-containing genomic sequence" is at least 15 contiguous nucleotides in length and contains at least one CpG pair. In some cases, it can be at least 18, 20, 25, 30, 50, 80, 100, 150, 200, 250, or 300 contiguous nucleotides in length and contains at least 2, 3, 4, 5, 6, 7, 8, 9, 10, 15, 20, 25, or 30 CpG pairs. In some instances, a CpG-containing genomic sequence is a segment (e.g., portion) of a gene that contains the promoter and exon 1 of the gene, wherein the segment can be at least 15, 18, 20, 25, 30, 50, 80, 100, 150, 200, 250, or 300 contiguous nucleotides in length. For example, a CpG-containing genomic sequence can be 300 to 3,000 base pairs in length. For any one "CpG-containing genomic sequence" at a given location, e.g., within a region of the human ZNF545 genomic sequence (such as the region containing the promoter and exon 1), nucleotide sequence variations may exist from individual to individual and from allele to allele even for the same individual. Furthermore, a "CpG-containing genomic sequence" may encompass a nucleotide sequence transcribed or not transcribed for protein production, and the nucleotide sequence can be a protein-coding sequence, a non protein-coding sequence (such as a transcription promoter), or a combination thereof.

The term "immunoglobulin" or "antibody" (used interchangeably herein) refers to an antigen-binding protein having a basic four-polypeptide chain structure consisting of two heavy and two light chains, said chains being stabilized, for example, by interchain disulfide bonds, which has the ability to specifically bind antigen. Both heavy and light chains are folded into domains.

The term "antibody" also refers to antigen- and epitope-binding fragments of antibodies, e.g., Fab fragments, that can be used in immunological affinity assays. There are a number of well characterized antibody fragments. Thus, for example, pepsin digests an antibody C-terminal to the disulfide linkages in the hinge region to produce $F(ab)'_2$, a dimer of Fab which itself is a light chain joined to $V_H$-$C_H1$ by a disulfide bond. The $F(ab)'_2$ can be reduced under mild conditions to break the disulfide linkage in the hinge region thereby converting the $(Fab')_2$ dimer into an Fab' monomer. The Fab' monomer is essentially a Fab with part of the hinge region (see, e.g., Fundamental Immunology, Paul, ed., Raven Press, N.Y. (1993), for a more detailed description of other antibody fragments). While various antibody fragments are defined in terms of the digestion of an intact antibody, one of skill will appreciate that fragments can be synthesized de novo either chemically or by utilizing recombinant DNA methodology. Thus, the term antibody also includes antibody fragments either produced by the modification of whole antibodies or synthesized using recombinant DNA methodologies.

The phrase "specifically binds," when used in the context of describing a binding relationship of a particular molecule to a protein or peptide, refers to a binding reaction that is determinative of the presence of the protein in a heterogeneous population of proteins and other biologics. Thus, under designated binding assay conditions, the specified binding agent (e.g., an antibody) binds to a particular protein at least two times the background and does not substantially bind in a significant amount to other proteins present in the sample. Specific binding of an antibody under such conditions may require an antibody that is selected for its specificity for a particular protein or a protein but not its similar "sister" proteins. A variety of immunoassay formats may be used to select antibodies specifically immunoreactive with a particular protein or in a particular form. For example, solid-phase ELISA immunoassays are routinely used to select antibodies specifically immunoreactive with a protein (see, e.g., Harlow & Lane, *Antibodies, A Laboratory Manual* (1988) for a description of immunoassay formats and conditions that can be used to determine specific immunoreactivity). Typically a specific or selective binding reaction will be at least twice background signal or noise and more typically more than 10 to 100 times background. On the other hand, the term "specifically bind" when used in the context of referring to a polynucleotide sequence forming a double-stranded complex with another polynucleotide sequence describes "polynucleotide hybridization" based on the Watson-Crick base-pairing, as provided in the definition for the term "polynucleotide hybridization method."

As used in this application, an "increase" or a "decrease" refers to a detectable positive or negative change in quantity from a comparison control, e.g., an established standard control (such as an average expression level of ZNF545 mRNA or protein found in non-cancerous stomach tissue). An increase is a positive change that is typically at least 10%, or at least 20%, or 50%, or 100%, and can be as high as at least 2-fold or at least 5-fold or even 10-fold of the control value. Similarly, a decrease is a negative change that is typically at least 10%, or at least 20%, 30%, or 50%, or even as high as at least 80% or 90% of the control value. Other terms indicating quantitative changes or differences from a comparative basis, such as "more," "less," "higher," and "lower," are used in this application in the same fashion as described above. In contrast, the term "substantially the same" or "substantially lack of change" indicates little to no change in quantity from the standard control value, typically within ±10% of the standard control, or within ±5%, 2%, or even less variation from the standard control.

A "polynucleotide hybridization method" as used herein refers to a method for detecting the presence and/or quantity of a pre-determined polynucleotide sequence based on its ability to form Watson-Crick base-pairing, under appropriate hybridization conditions, with a polynucleotide probe of a known sequence. Examples of such hybridization methods include Southern blot, Northern blot, microarray and in situ hybridization. A polynucleotide probe can be conjugated with a chemical moiety that generates a detectable fluorescent signal, such as but not limited to, a fluorescent moiety or a fluorochrome. In some cases, the probe is a molecular beacon.

"Primers" as used herein refer to oligonucleotides that can be used in an amplification method, such as a polymerase chain reaction (PCR), to amplify a nucleotide sequence based on the polynucleotide sequence corresponding to a gene of interest, e.g., the cDNA or genomic sequence for human ZNF545 or a portion thereof. Typically at least one of the PCR primers for amplification of a polynucleotide sequence is sequence-specific for that polynucleotide sequence. The exact length of the primer will depend upon many factors, including temperature, source of the primer, and the method used. For example, for diagnostic and prognostic applications, depending on the complexity of the target sequence, the oligonucleotide primer typically contains at least 10, or 15, or 20, or 25 or more nucleotides, although it may contain fewer nucleotides or more nucleotides. The factors involved in determining the appropriate length of primer are readily known to one of ordinary skill in the art. The primers used in particular embodiments are shown in Table 1 of the disclosure where their specific applications are indicated. In this disclosure the term "primer pair" means a pair of primers that hybridize to opposite strands a target DNA molecule or to regions of the target DNA which flank a nucleotide sequence to be amplified. In this disclosure the term "primer site", means the area of the target DNA or other nucleic acid to which a primer hybridizes.

A "label," "detectable label," or "detectable moiety" is a composition detectable by spectroscopic, photochemical, biochemical, immunochemical, chemical, or other physical means. For example, useful labels include $^{32}$P, fluorescent dyes, electron-dense reagents, enzymes (e.g., as commonly used in an ELISA), biotin, digoxigenin, or haptens and proteins that can be made detectable, e.g., by incorporating a radioactive component into the peptide or used to detect antibodies specifically reactive with the peptide. Typically a detectable label is attached to a probe or a molecule with defined binding characteristics (e.g., a polypeptide with a known binding specificity or a polynucleotide), so as to allow the presence of the probe (and therefore its binding target) to be readily detectable.

"Standard control" as used herein refers to a predetermined amount or concentration of a polynucleotide sequence or polypeptide, e.g., ZNF545 mRNA or protein, that is present in an established normal disease-free tissue sample, e.g., a normal stomach epithelial tissue sample. The standard control value is suitable for the use of a method of the present invention, to serve as a basis for comparing the amount of ZNF545 mRNA or protein that is present in a test sample. An established sample serving as a standard control provides an average amount of ZNF545 mRNA or protein that is typical for a stomach epithelial tissue sample (e.g., stomach mucosa) of an average, healthy human without any stomach disease especially gastric cancer as conventionally defined. A standard control value may vary depending on the nature of the sample as well as other factors such as the gender, age, ethnicity of the subjects based on whom such a control value is established.

The term "average," as used in the context of describing a human who is healthy, free of any stomach disease (especially gastric cancer) as conventionally defined, refers to certain characteristics, especially the amount of human ZNF545 mRNA or ZNF545 protein, found in the person's stomach tissue, e.g., epithelial tissue or gastric mucosa, that are representative of a randomly selected group of healthy humans who are free of any stomach diseases (especially gastric cancer). This selected group should comprise a sufficient number of humans such that the average amount of ZNF545 mRNA or protein in the stomach mucosa among these individuals reflects, with reasonable accuracy, the corresponding amount of ZNF545 mRNA/protein in the general population of healthy humans. In addition, the selected group of humans generally have a similar age to that of a subject whose stomach tissue sample is tested for indication of gastric cancer. Moreover, other factors such as gender, ethnicity, medical history are also considered and preferably closely matching between the profiles of the test subject and the selected group of individuals establishing the "average" value.

The term "amount" as used in this application refers to the quantity of a polynucleotide of interest or a polypeptide of interest, e.g., human ZNF545 mRNA or protein, present in a sample. Such quantity may be expressed in the absolute terms, i.e., the total quantity of the polynucleotide or polypeptide in the sample, or in the relative terms, i.e., the concentration of the polynucleotide or polypeptide in the sample.

The term "treat" or "treating," as used in this application, describes to an act that leads to the elimination, reduction, alleviation, reversal, or prevention or delay of onset or recurrence of any symptom of a relevant condition. In other words, "treating" a condition encompasses both therapeutic and prophylactic intervention against the condition.

The term "effective amount" as used herein refers to an amount of a given substance that is sufficient in quantity to produce a desired effect. For example, an effective amount of an polynucleotide encoding ZNF545 mRNA is the amount of said polynucleotide to achieve an increased level of ZNF545 protein expression or biological activity, such that the symptoms of gastric cancer are reduced, reversed, eliminated, prevented, or delayed of the onset in a patient who has been given the polynucleotide for therapeutic purposes. An amount adequate to accomplish this is defined as the "therapeutically effective dose." The dosing range varies with the nature of the therapeutic agent being administered and other factors such as the route of administration and the severity of a patient's condition.

The term "subject" or "subject in need of treatment," as used herein, includes individuals who seek medical attention due to risk of, or actual suffering from, gastric cancer. Subjects also include individuals currently undergoing therapy that seek manipulation of the therapeutic regimen. Subjects or individuals in need of treatment include those that demonstrate symptoms of gastric cancer or are at risk of suffering from gastric cancer or its symptoms. For example, a subject in need of treatment includes individuals with a genetic predisposition or family history for gastric cancer, those that have suffered relevant symptoms in the past, those that have been exposed to a triggering substance or event, as well as those suffering from chronic or acute symptoms of the condition. A "subject in need of treatment" may be at any age of life.

"Inhibitors," "activators," and "modulators" of ZNF545 protein are used to refer to inhibitory, activating, or modulating molecules, respectively, identified using in vitro and in vivo assays for ZNF545 protein binding or signaling, e.g., ligands, agonists, antagonists, and their homologs and mimetics. The term "modulator" includes inhibitors and activators. Inhibitors are agents that, e.g., partially or totally block carbohydrate binding, decrease, prevent, delay activation, inactivate, desensitize, or down regulate the activity of ZNF545 protein. In some cases, the inhibitor directly or indirectly binds to ZNF545 protein, such as a neutralizing antibody Inhibitors, as used herein, are synonymous with inactivators and antagonists. Activators are agents that, e.g., stimulate, increase, facilitate, enhance activation, sensitize or up regulate the activity of ZNF545 protein. Modulators include ZNF545 protein ligands or binding partners, including modifications of naturally-occurring ligands and synthetically-designed ligands, antibodies and antibody fragments, antagonists, agonists, small molecules including carbohydrate-containing molecules, siRNAs, RNA aptamers, and the like.

I. Introduction

Gastric cancer patients often face a grim prognosis due to the nature of this disease in its lacking of specific symptoms during its early development stages. Early detection of gastric cancer is therefore critical for improving patient survival rate.

The present inventors discovered for the first time that expression of ZNF545 protein is suppressed in gastric cancer cells. This suppressed expression of ZNF545 protein is due to increased methylation in the ZNF545 genomic sequence, especially in the promoter region of the gene, which leads to decreased transcription of ZNF545 mRNA. This discovery provides important means for detecting, monitoring, and treating gastric cancer.

II. General Methodology

Practicing this invention utilizes routine techniques in the field of molecular biology. Basic texts disclosing the general methods of use in this invention include Sambrook and Russell, *Molecular Cloning, A Laboratory Manual* (3rd ed. 2001); Kriegler, *Gene Transfer and Expression: A Laboratory Manual* (1990); and *Current Protocols in Molecular Biology* (Ausubel et al., eds., 1994)).

For nucleic acids, sizes are given in either kilobases (kb) or base pairs (bp). These are estimates derived from agarose or acrylamide gel electrophoresis, from sequenced nucleic acids, or from published DNA sequences. For proteins, sizes are given in kilodaltons (kDa) or amino acid residue numbers. Protein sizes are estimated from gel electrophoresis, from sequenced proteins, from derived amino acid sequences, or from published protein sequences.

Oligonucleotides that are not commercially available can be chemically synthesized, e.g., according to the solid phase phosphoramidite triester method first described by Beaucage and Caruthers, *Tetrahedron Lett.* 22:1859-1862 (1981), using an automated synthesizer, as described in Van Devanter et. al., *Nucleic Acids Res.* 12:6159-6168 (1984). Purification of oligonucleotides is performed using any art-recognized strategy, e.g., native acrylamide gel electrophoresis or anion-exchange high performance liquid chromatography (HPLC) as described in Pearson and Reanier, *J. Chrom.* 255: 137-149 (1983).

The sequence of interest used in this invention, e.g., the polynucleotide sequence of the human ZNF545 gene, and synthetic oligonucleotides (e.g., primers) can be verified using, e.g., the chain termination method for sequencing double-stranded templates of Wallace et al., *Gene* 16: 21-26 (1981).

A. Acquisition and Preparation of Stomach Tissue Samples

A stomach tissue sample is obtained from a person to be tested or monitored for gastric cancer using a method of the present invention. The stomach tissue sample can be a cancer (tumor) sample or a non-cancer sample. Collection of stomach epithelial tissue (e.g., stomach mucosal tissue) sample from an individual is performed in accordance with the standard protocol hospitals or clinics generally follow, such as during an endoscopy. An appropriate amount of stomach epithelium is collected and may be stored according to standard procedures prior to further preparation.

The analysis of ZNF545 mRNA or DNA found in a patient's stomach epithelial sample according to the present invention may be performed using, e.g., stomach mucosa. The methods for preparing tissue samples for nucleic acid extraction are well known among those of skill in the art. For example, a subject's stomach mucosa sample should be first treated to disrupt cellular membrane so as to release nucleic acids contained within the cells.

B. Extraction and Quantitation of RNA

There are numerous methods for extracting mRNA from a biological sample. The general methods of mRNA preparation (e.g., described by Sambrook and Russell, *Molecular Cloning: A Laboratory Manual* 3d ed., 2001) can be followed; various commercially available reagents or kits, such as Trizol reagent (Invitrogen, Carlsbad, Calif.), Oligotex Direct mRNA Kits (Qiagen, Valencia, Calif.), RNeasy Mini Kits (Qiagen, Hilden, Germany), and PolyATtract® Series 9600™ (Promega, Madison, Wis.), may also be used to obtain mRNA from a biological sample from a test subject. Combinations of more than one of these methods may also be used.

It is essential that all contaminating DNA be eliminated from the RNA preparations. Thus, careful handling of the samples, thorough treatment with DNase, and proper negative controls in the amplification and quantification steps should be used.

1. PCR-Based Quantitative Determination of mRNA Level

Once mRNA is extracted from a sample, the amount of human ZNF545 may be quantified. The preferred method for determining the mRNA level is an amplification-based method, e.g., by polymerase chain reaction (PCR), especially reverse transcription-polymerase chain reaction (RT-PCR).

Prior to the amplification step, a DNA copy (cDNA) of the human ZNF545 must be synthesized. This is achieved by reverse transcription, which can be carried out as a separate step, or in a homogeneous reverse transcription-polymerase chain reaction (RT-PCR), a modification of the polymerase chain reaction for amplifying RNA. Methods suitable for PCR amplification of ribonucleic acids are described by Romero and Rotbart in *Diagnostic Molecular Biology: Principles and Applications* pp. 401-406; Persing et al., eds., Mayo Foundation, Rochester, Minn., 1993; Egger et al., *J. Clin. Microbiol.* 33:1442-1447, 1995; and U.S. Pat. No. 5,075,212.

The general methods of PCR are well known in the art and are thus not described in detail herein. For a review of PCR methods, protocols, and principles in designing primers, see, e.g., Innis, et al., *PCR Protocols: A Guide to Methods and Applications*, Academic Press, Inc. N.Y., 1990. PCR reagents and protocols are also available from commercial vendors, such as Roche Molecular Systems.

PCR is most usually carried out as an automated process with a thermostable enzyme. In this process, the temperature of the reaction mixture is cycled through a denaturing region, a primer annealing region, and an extension reaction region automatically. Machines specifically adapted for this purpose are commercially available.

Although PCR amplification of the target mRNA is typically used in practicing the present invention. One of skill in the art will recognize, however, that amplification of these mRNA species in a maternal blood sample may be accomplished by any known method, such as ligase chain reaction (LCR), transcription-mediated amplification, and self-sustained sequence replication or nucleic acid sequence-based amplification (NASBA), each of which provides sufficient amplification. More recently developed branched-DNA technology may also be used to quantitatively determining the amount of mRNA markers in maternal blood. For a review of branched-DNA signal amplification for direct quantitation of nucleic acid sequences in clinical samples, see Nolte, *Adv. Clin. Chem.* 33:201-235, 1998.

2. Other Quantitative Methods

The ZNF545 mRNA can also be detected using other standard techniques, well known to those of skill in the art.

Although the detection step is typically preceded by an amplification step, amplification is not required in the methods of the invention. For instance, the mRNA may be identified by size fractionation (e.g., gel electrophoresis), whether or not proceeded by an amplification step. After running a sample in an agarose or polyacrylamide gel and labeling with ethidium bromide according to well known techniques (see, e.g., Sambrook and Russell, supra), the presence of a band of the same size as the standard comparison is an indication of the presence of a target mRNA, the amount of which may then be compared to the control based on the intensity of the band. Alternatively, oligonucleotide probes specific to ZNF545 mRNA can be used to detect the presence of such mRNA species and indicate the amount of mRNA in comparison to the standard comparison, based on the intensity of signal imparted by the probe.

Sequence-specific probe hybridization is a well known method of detecting a particular nucleic acid comprising other species of nucleic acids. Under sufficiently stringent hybridization conditions, the probes hybridize specifically only to substantially complementary sequences. The stringency of the hybridization conditions can be relaxed to tolerate varying amounts of sequence mismatch.

A number of hybridization formats well known in the art, including but not limited to, solution phase, solid phase, or mixed phase hybridization assays. The following articles provide an overview of the various hybridization assay formats: Singer et al., *Biotechniques* 4:230, 1986; Haase et al., *Methods in Virology*, pp. 189-226, 1984; Wilkinson, *In situ Hybridization*, Wilkinson ed., IRL Press, Oxford University Press, Oxford; and Hames and Higgins eds., *Nucleic Acid Hybridization: A Practical Approach*, IRL Press, 1987.

The hybridization complexes are detected according to well known techniques. Nucleic acid probes capable of specifically hybridizing to a target nucleic acid, i.e., the mRNA or the amplified DNA, can be labeled by any one of several methods typically used to detect the presence of hybridized nucleic acids. One common method of detection is the use of autoradiography using probes labeled with $^{3}H$, $^{125}I$, $^{35}S$, $^{14}C$, $^{5}C$ or $^{32}P$, or the like. The choice of radioactive isotope depends on research preferences due to ease of synthesis, stability, and half-lives of the selected isotopes. Other labels include compounds (e.g., biotin and digoxigenin), which bind to antiligands or antibodies labeled with fluorophores, chemiluminescent agents, and enzymes. Alternatively, probes can be conjugated directly with labels such as fluorophores, chemiluminescent agents or enzymes. The choice of label depends on sensitivity required, ease of conjugation with the probe, stability requirements, and available instrumentation.

The probes and primers necessary for practicing the present invention can be synthesized and labeled using well known techniques. Oligonucleotides used as probes and primers may be chemically synthesized according to the solid phase phosphoramidite triester method first described by Beaucage and Caruthers, *Tetrahedron Letts.*, 22:1859-1862, 1981, using an automated synthesizer, as described in Needham-VanDevanter et al., *Nucleic Acids Res.* 12:6159-6168, 1984. Purification of oligonucleotides is by either native acrylamide gel electrophoresis or by anion-exchange HPLC as described in Pearson and Regnier, *J. Chrom.*, 255: 137-149, 1983.

C. Detection of Methylation in ZNF545 Genomic Sequence

Methylation status of a segment of ZNF545 genomic sequence containing one or more CpG (cytosine-guanine dinucleotide) pairs is investigated to provide indication as to whether a test subject is suffering from gastric cancer, whether the subject is at risk of developing gastric cancer, or whether the subject's gastric cancer is worsening or improving.

Typically a segment of the ZNF545 genomic sequence that includes the 5' untranslated region (such as the promoter region) and includes one or more CpG nucleotide pairs is analyzed for methylation pattern. For example, SEQ ID NO:1 or 2 or a portion thereof can be used to determine how many of the CpG pairs within the sequence are methylated and how many are not methylated. The sequence being analyzed should be long enough to contain at least 1 CpG dinucleotide pair and detection of methylation at this CpG site is typically adequate indication of the presence of gastric cancer cells. The length of the sequence being analyzed is usually at least 15 or 20 contiguous nucleotides, and may be longer with at least 25, 30, 50, 100, 200, 300, 400, or more contiguous nucleotides. At least one, typically 2 or more, often 3, 4, 5, 6, 7, 8, 9, or more, CpG nucleotide pairs are present within the sequence. In the cases of multiple (2 or more) CpG sites are analyzed for methylation status, when at least 50% of the CpG pairs within the analyzed genomic sequence are shown to be methylated, subject being tested is deemed to have gastric cancer or have an elevated risk of developing gastric cancer. As an example, SEQ ID NO:1, a segment of ZNF545 genomic sequence, and SEQ ID NO:2, a segment of ZNF545 genomic, contain several CpG pairs. Some or majority of the CpG pairs in this region are found to be methylated in established gastric cancer cell lines and samples taken from gastric cancer, whereas non-cancerous stomach epithelial cells showed very few, if any at all, methylated CpG sites. For the purpose of determining the methylation pattern of a ZNF545 genomic sequence, bisulfite treatment followed by DNA sequencing is particularly useful, since bisulfite converts an unmethylated cytosine (C) to a uracil (U) while leaving methylated cytosines unchanged, allowing immediate identification through a DNA sequencing process. Optionally, an amplification process such as PCR is included after the bisulfite conversion and before the DNA sequencing.

1. DNA Extraction and Treatment

Methods for extracting DNA from a biological sample are well known and routinely practiced in the art of molecular biology, see, e.g., Sambrook and Russell, supra. RNA contamination should be eliminated to avoid interference with DNA analysis. The DNA is then treated with a reagent capable of modifying DNA in a methylation differential manner, i.e., different and distinguishable chemical structures will result from a methylated cytosine (C) residue and an unmethylated C residue following the treatment. Typically, such a reagent reacts with the unmethylated C residue(s) in a DNA molecule and converts each unmethylated C residue to a uracil (U) residue, whereas the methylated C residues remain unchanged. This unmethylated C→U conversion allows detection and comparison of methylation status based on changes in the primary sequence of the nucleic acid. An exemplary reagent suitable for this purpose is bisulfite, such as sodium bisulfite. Methods for using bisulfite for chemical modification of DNA are well known in the art (see, e.g., Herman et al., *Proc. Natl. Acad. Sci. USA* 93:9821-9826, 1996).

As a skilled artisan will recognize, any other reagents that are unnamed here but have the same property of chemically (or through any other mechanism) modifying methylated and unmethylated DNA differentially can be used for practicing the present invention. For instance, methylation-specific modification of DNA may also be accomplished by methylation-sensitive restriction enzymes, some of which typically cleave an unmethylated DNA fragment but not a methylated DNA fragment, while others (e.g., methylation-dependent endonuclease McrBC) cleave DNA containing methylated cytosines but not unmethylated DNA. In addition, a combination of chemical modification and restriction enzyme treatment, e.g., combined bisulfite restriction analysis (COBRA) (Xiong et al. 1997 *Nucleic Acids Res.* 25(12): 2532-2534), is useful for practicing the present invention. Other available methods for detecting DNA methylation include, for example, methylation-sensitive restriction endonucleases (MSREs) assay by either Southern blot or PCR analysis, methylation specific or methylation sensitive-PCR (MSP), methylation-sensitive single nucleotide primer extension (Ms-SnuPE), high resolution melting (HRM) analysis, bisulifte sequencing, pyrosequencing, methylation-specific single-strand conformation analysis (MS-SSCA), methylation-specific denaturing gradient gel electrophoresis (MS-DGGE), methylation-specific melting curve analysis (MS-MCA), methylation-specific denaturing high-performance liquid chromatography (MS-DHPLC), methylation-specific microarray (MSO). These assays can be either PCR analysis, quantitative analysis with fluorescence labelling or Southern blot analysis. Exemplary methylation sensitive DNA cleaving reagent such as restriction enzymes include AatII, AciI, AclI, AgeI, AscI, Asp718, AvaI, BbrP1, BceAI, BmgBI, BsaAI, BsaHI, BsiEI, BsiWI, BsmBI, BspDI, BsrFI, BssHII, BstBI, BstUI, ClaI, EagI, EagI-HF™, FauI, FseI, FspI, HaeII, HgaI, HhaI, HinP1I, HpaII, Hpy99I, HpyCH4IV, KasI, MluI, NarI, NgoMIV, NotI, NotI-HF™, NruI, Nt.BsmAI, PaeR7I, PspXI, PvuI, RsrII, SacII, SalI, SalI-HF™, SfoI, SgrAI, SmaI, SnaBI or TspMI. A methylation sensitive DNA cleaving reagent includes an enzyme that preferentially cleaves methylated DNA (e.g., MspJI) and an enzyme that preferentially cleaves unmethylated DNA (e.g., HpaII). Detailed description of MSP is found in, e.g., Herman et al., *Proc. Natl. Acad, Sci. USA,* 1996, 93:9821-9826.

2. Optional Amplification and Sequence Analysis

Following the modification of DNA in a methylation-differential manner, the treated DNA is then subjected to sequence-based analysis, such that the methylation status of the ZNF545 genomic sequence may be determined. An amplification reaction is optional prior to the sequence analysis after methylation specific modification. A variety of polynucleotide amplification methods are well established and frequently used in research. For instance, the general methods of polymerase chain reaction (PCR) for polynucleotide sequence amplification are well known in the art and are thus not described in detail herein. For a review of PCR methods, protocols, and principles in designing primers, see, e.g., Innis, et al., *PCR Protocols: A Guide to Methods and Applications*, Academic Press, Inc. N.Y., 1990. PCR reagents and protocols are also available from commercial vendors, such as Roche Molecular Systems.

Although PCR amplification is typically used in practicing the present invention, one of skill in the art will recognize that amplification of the relevant genomic sequence may be accomplished by any known method, such as the ligase chain reaction (LCR), transcription-mediated amplification, and self-sustained sequence replication or nucleic acid sequence-based amplification (NASBA), each of which provides sufficient amplification.

Techniques for polynucleotide sequence determination are also well established and widely practiced in the relevant research field. For instance, the basic principles and general techniques for polynucleotide sequencing are described in various research reports and treatises on molecular biology and recombinant genetics, such as Wallace et al., supra; Sambrook and Russell, supra, and Ausubel et al., supra. DNA sequencing methods routinely practiced in research laboratories, either manual or automated, can be used for practicing the present invention. Additional means suitable for detecting changes (e.g., C→U) in a polynucleotide sequence for practicing the methods of the present invention include but are not limited to mass spectrometry, primer extension, polynucleotide hybridization, real-time PCR, melting curve analysis, high resolution melting analysis, heteroduplex analysis, pyrosequencing, and electrophoresis.

IV. Quantitation of Polypeptides

A. Obtaining Samples

The first step of practicing the present invention is to obtain a sample of stomach epithelium (e.g., stomach mucosa) from a subject being tested, assessed, or monitored for gastric cancer, the risk of developing gastric cancer, or the severity/progression of the condition. Samples of the same type should be taken from both a control group (normal individuals not suffering from any stomach disorder especially neoplasia) and a test group (subjects being tested for possible gastric cancer, for example). Standard procedures routinely employed in hospitals or clinics are typically followed for this purpose, as stated in the previous section.

For the purpose of detecting the presence of gastric cancer or assessing the risk of developing gastric cancer in test subjects, individual patients' stomach mucosa samples may be taken and the level of human ZNF545 protein may be measured and then compared to a standard control. If a decrease in the level of human ZNF545 protein is observed when compared to the control level, the test subject is deemed to have gastric cancer or have an elevated risk of developing the condition. For the purpose of monitoring disease progression or assessing therapeutic effectiveness in gastric cancer patients, individual patient's stomach epithelial samples may be taken at different time points, such that the level of human ZNF545 protein can be measured to provide information indicating the state of disease. For instance, when a patient's ZNF545 protein level shows a general trend of increase over time, the patient is deemed to be improving in the severity of gastric cancer or the therapy the patient has been receiving is deemed effective. A lack of change in a patient's ZNF545 protein level or a continuing trend of decrease on other hand would indicate a worsening of the condition and ineffectiveness of the therapy given to the patient. Generally, a lower ZNF545 protein level seen in a patient indicates a more severe form of the gastric cancer the patient is suffering from and a worse prognosis of the disease, as manifested in shorter life expectancy, higher rate of metastasis, resistance to therapy etc.

B. Preparing Samples for ZNF545 Protein Detection

The gastric (stomach) tissue sample from a subject is suitable for the present invention and can be obtained by well-known methods and as described in the previous section. In certain applications of this invention, stomach epithelial tissue (e.g., stomach mucosal tissue) may be the preferred sample type. In some instances, the gastric tissue sample is a gastric cancer sample containing a gastric cancer cell.

C. Determining the Level of Human ZNF545 Protein

A protein of any particular identity, such as ZNF545 protein, can be detected using a variety of immunological assays. In some embodiments, a sandwich assay can be performed by capturing the polypeptide from a test sample with an antibody having specific binding affinity for the polypeptide. The polypeptide then can be detected with a labeled antibody having specific binding affinity for it. Such immunological assays can be carried out using microfluidic devices such as microarray protein chips. A protein of interest (e.g., human ZNF545 protein) can also be detected by gel electrophoresis (such as 2-dimensional gel electrophoresis) and western blot analysis using specific antibodies. Alternatively, standard immunohistochemical techniques can be used to detect a given protein (e.g., human ZNF545 protein), using the appropriate antibodies. Both monoclonal and polyclonal antibodies (including antibody fragment with desired binding specificity) can be used for specific detection of the polypeptide. Such antibodies and their binding fragments with specific binding affinity to a particular protein (e.g., human ZNF545 protein) can be generated by known techniques.

Other methods may also be employed for measuring the level of ZNF545 protein in practicing the present invention. For instance, a variety of methods have been developed based on the mass spectrometry technology to rapidly and accurately quantify target proteins even in a large number of samples. These methods involve highly sophisticated equipment such as the triple quadrupole (triple Q) instrument using the multiple reaction monitoring (MRM) technique, matrix assisted laser desorption/ionization time-of-flight tandem mass spectrometer (MALDI TOF/TOF), an ion trap instrument using selective ion monitoring SIM) mode, and the electrospray ionization (ESI) based QTOP mass spectrometer. See, e.g., Pan et al., *J Proteome Res.* 2009 February; 8(2):787-797.

V. Establishing a Standard Control

In order to establish a standard control for practicing the method of this invention, a group of healthy persons free of any stomach disease (especially any form of tumor such as gastric cancer) as conventionally defined is first selected. These individuals are within the appropriate parameters, if applicable, for the purpose of screening for and/or monitoring gastric cancer using the methods of the present invention. Optionally, the individuals are of same gender, similar age, or similar ethnic background.

The healthy status of the selected individuals is confirmed by well established, routinely employed methods including but not limited to general physical examination of the individuals and general review of their medical history.

Furthermore, the selected group of healthy individuals must be of a reasonable size, such that the average amount/concentration of human ZNF545 mRNA or ZNF545 protein in the stomach tissue sample obtained from the group can be reasonably regarded as representative of the normal or average level among the general population of healthy people. Preferably, the selected group comprises at least 10 human subjects.

Once an average value for the ZNF545 mRNA or ZNF545 protein is established based on the individual values found in each subject of the selected healthy control group, this average or median or representative value or profile is considered a standard control. A standard deviation is also determined during the same process. In some cases, separate standard controls may be established for separately defined groups having distinct characteristics such as age, gender, or ethnic background.

VI. Treatment of Gastric Cancer

By illustrating the correlation of suppressed expression of ZNF545 protein and gastric cancer, the present invention further provides a means for treating patients suffering from gastric cancer: by way of increasing ZNF545 protein expression or biological activity. As used herein, treatment of gastric cancer encompasses reducing, reversing, lessening, or eliminating one or more of the symptoms of gastric cancer, as well as preventing or delaying the onset of one or more of the relevant symptoms.

A. Increasing ZNF545 Expression or Activity

1. Nucleic Acids Encoding ZNF545 Proteins

Enhancement of ZNF545 gene expression can be achieved through the use of nucleic acids encoding a functional ZNF545 protein. Such nucleic acids can be single-stranded nucleic acids (such as mRNA) or double-stranded nucleic acids (such as DNA) that can translate into an active form of ZNF545 protein under favorable conditions.

In one embodiment, the ZNF545-encoding nucleic acid is provided in the form of an expression cassette, typically recombinantly produced, having a promoter operably linked to the polynucleotide sequence encoding the ZNF545 protein. In some cases, the promoter is a universal promoter that directs gene expression in all or most tissue types; in other cases, the promoter is one that directs gene expression specifically in epithelial cells, especially in stomach epithelium. Administration of such nucleic acids can increase the ZNF545 protein expression in the target tissue, e.g., stomach epithelium. Since the human ZNF545 gene cDNA sequence is known as Genbank Accession No.: NM_133466 and provided herein as SEQ ID NO:4, one can derive a suitable ZNF545-encoding nucleic acid from the sequence, species homologs, and variants of these sequences.

2. ZNF545 Proteins

By directly administering an effective amount of an active ZNF545 protein to a patient suffering from gastric cancer and exhibiting suppressed ZNF545 protein expression or activity, the disease may also be effectively treated. For example, this can be achieved by administering a recombinantly produced ZNF545 protein possessing its biological activity to the patient suffering from gastric cancer. Formulations and methods for delivering a protein- or polypeptide-based therapeutic agent are well known in the art.

3. Activators of ZNF545 Protein

Increased ZNF545 protein activity can be achieved with an agent that is capable of activating the expression of ZNF545 protein or enhancing the activity of ZNF545 protein. For example, a demethylating agent (e.g., 5-azacytidine or 5-azadeoxycytidine) may be able to activate ZNF545 gene expression by removing the suppression of ZNF545 gene expression caused by methylation of the promoter region of this gene. Other activating agents may include transcriptional activators specific for the ZNF545 promoter and/or enhancer. Such activating agents can be screened for and identified using the ZNF545 expression assays described in the examples herein.

Agonists of the ZNF545 protein, such as an activating antibody, are another kind of activators of the ZNF545 protein. Such activators act by enhancing the biological activity of the ZNF545 protein, typically (but not necessarily) by direct binding with the ZNF545 protein and/or its interacting proteins. Preliminary screening for such agonists may start with a binding assay for identifying molecules that physically interact with ZNF545 protein.

B. Pharmaceutical Compositions

1. Formulations

Compounds of the present invention are useful in the manufacture of a pharmaceutical composition or a medicament. A pharmaceutical composition or medicament can be administered to a subject for the treatment of gastric cancer.

Compounds used in the present invention, e.g., a ZNF545 protein, a nucleic acid encoding ZNF545 protein, or an activator of ZNF545 gene expression, are useful in the manufacture of a pharmaceutical composition or a medicament comprising an effective amount thereof in conjunction or mixture with excipients or carriers suitable for application.

An exemplary pharmaceutical composition for enhancing ZNF545 expression comprises (i) an express cassette comprising a polynucleotide sequence encoding a human ZNF545 protein as described herein, and (ii) a pharmaceutically acceptable excipient or carrier. The terms pharmaceutically-acceptable and physiologically-acceptable are used synonymously herein. The expression cassette may be provided in a therapeutically effective dose for use in a method for treatment as described herein.

A ZNF545 protein or a nucleic acid encoding a ZNF545 protein can be administered via liposomes, which serve to target the conjugates to a particular tissue, as well as increase the half-life of the composition. Liposomes include emulsions, foams, micelles, insoluble monolayers, liquid crystals, phospholipid dispersions, lamellar layers and the like. In these preparations the inhibitor to be delivered is incorporated as part of a liposome, alone or in conjunction with a molecule which binds to, e.g., a receptor prevalent among the targeted cells (e.g., skin cells), or with other therapeutic or immunogenic compositions. Thus, liposomes filled with a desired inhibitor of the invention can be directed to the site of treatment, where the liposomes then deliver the selected inhibitor compositions. Liposomes for use in the invention are formed from standard vesicle-forming lipids, which generally include neutral and negatively charged phospholipids and a sterol, such as cholesterol. The selection of lipids is generally guided by consideration of, e.g., liposome size, acid lability and stability of the liposomes in the blood stream. A variety of methods are available for preparing liposomes, as described in, e.g., Szoka et al. (1980) Ann. Rev. Biophys. Bioeng. 9: 467, U.S. Pat. Nos. 4,235,871, 4,501,728 and 4,837,028.

Pharmaceutical compositions or medicaments for use in the present invention can be formulated by standard techniques using one or more physiologically acceptable carriers or excipients. Suitable pharmaceutical carriers are described herein and in "Remington's Pharmaceutical Sciences" by E. W. Martin. Compounds and agents of the present invention and their physiologically acceptable salts and solvates can be formulated for administration by any suitable route, including via inhalation, topically, nasally, orally, parenterally, or rectally.

Typical formulations for topical administration include creams, ointments, sprays, lotions, and patches. The pharmaceutical composition can, however, be formulated for any type of administration, e.g., intradermal, subdermal, intravenous, intramuscular, intranasal, intracerebral, intratracheal, intraarterial, intraperitoneal, intravesical, intrapleural, intracoronary or intratumoral injection, with a syringe or other devices. Formulation for administration by inhalation (e.g., aerosol), or for oral, rectal, or vaginal administration is also contemplated.

2. Routes of Administration

Suitable formulations for topical application, e.g., to the skin and eyes, are preferably aqueous solutions, ointments, creams or gels well-known in the art. Such may contain solubilizers, stabilizers, tonicity enhancing agents, buffers and preservatives.

Suitable formulations for transdermal application include an effective amount of a compound or agent of the present invention with carrier. Preferred carriers include absorbable pharmacologically acceptable solvents to assist passage through the skin of the host. For example, transdermal devices are in the form of a bandage comprising a backing member, a reservoir containing the compound optionally with carriers, optionally a rate controlling barrier to deliver the compound to the skin of the host at a controlled and predetermined rate over a prolonged period of time, and means to secure the device to the skin. Matrix transdermal formulations may also be used.

For oral administration, a pharmaceutical composition or a medicament can take the form of, for example, a tablet or a capsule prepared by conventional means with a pharmaceutically acceptable excipient. Preferred are tablets and gelatin capsules comprising the active ingredient, i.e., a ZNF545 protein or a nucleic acid encoding a ZNF545 protein, together with (a) diluents or fillers, e.g., lactose, dextrose, sucrose, mannitol, sorbitol, cellulose (e.g., ethyl cellulose, microcrystalline cellulose), glycine, pectin, polyacrylates and/or calcium hydrogen phosphate, calcium sulfate, (b) lubricants, e.g., silica, talcum, stearic acid, its magnesium or calcium salt, metallic stearates, colloidal silicon dioxide, hydrogenated vegetable oil, corn starch, sodium benzoate, sodium acetate and/or polyethyleneglycol; for tablets also (c) binders, e.g., magnesium aluminum silicate, starch paste, gelatin, tragacanth, methylcellulose, sodium carboxymethylcellulose, polyvinylpyrrolidone and/or hydroxypropyl methylcellulose; if desired (d) disintegrants, e.g., starches (e.g., potato starch or sodium starch), glycolate, agar, alginic acid or its sodium salt, or effervescent mixtures; (e) wetting agents, e.g., sodium lauryl sulphate, and/or (f) absorbents, colorants, flavors and sweeteners.

Tablets may be either film coated or enteric coated according to methods known in the art. Liquid preparations for oral administration can take the form of, for example, solutions, syrups, or suspensions, or they can be presented as a dry product for constitution with water or other suitable vehicle before use. Such liquid preparations can be prepared by conventional means with pharmaceutically acceptable additives, for example, suspending agents, for example, sorbitol syrup, cellulose derivatives, or hydrogenated edible fats; emulsifying agents, for example, lecithin or acacia; non-aqueous vehicles, for example, almond oil, oily esters, ethyl alcohol, or fractionated vegetable oils; and preservatives, for example, methyl or propyl-p-hydroxybenzoates or sorbic acid. The preparations can also contain buffer salts, flavoring, coloring, and/or sweetening agents as appropriate. If desired, preparations for oral administration can be suitably formulated to give controlled release of the active compound.

Compounds and agents of the present invention can be formulated for parenteral administration by injection, for example by bolus injection or continuous infusion. Formulations for injection can be presented in unit dosage form, for example, in ampoules or in multi-dose containers, with an added preservative. Injectable compositions are preferably aqueous isotonic solutions or suspensions, and suppositories are preferably prepared from fatty emulsions or suspensions. The compositions may be sterilized and/or contain adjuvants, such as preserving, stabilizing, wetting or emulsifying agents, solution promoters, salts for regulating the osmotic pressure and/or buffers. Alternatively, the active ingredient can be in powder form for constitution with a suitable vehicle, for example, sterile pyrogen-free water, before use. In addition, they may also contain other therapeutically valuable substances. The compositions are prepared according to conventional mixing, granulating or coating methods, respectively, and contain about 0.1 to 75%, preferably about 1 to 50%, of the active ingredient.

For administration by inhalation, the active ingredient, e.g., a ZNF545 protein or a nucleic acid encoding a ZNF545 protein, may be conveniently delivered in the form of an aerosol spray presentation from pressurized packs or a nebulizer, with the use of a suitable propellant, for example, dichlorodifluoromethane, trichlorofluoromethane, dichlorotetrafluoroethane, carbon dioxide, or other suitable gas. In the case of a pressurized aerosol, the dosage unit can be determined by providing a valve to deliver a metered amount. Capsules and cartridges of, for example, gelatin for use in an inhaler or insufflator can be formulated containing a powder mix of the compound and a suitable powder base, for example, lactose or starch.

The inhibitors can also be formulated in rectal compositions, for example, suppositories or retention enemas, for example, containing conventional suppository bases, for example, cocoa butter or other glycerides.

Furthermore, the active ingredient can be formulated as a depot preparation. Such long-acting formulations can be administered by implantation (for example, subcutaneously or intramuscularly) or by intramuscular injection. Thus, for example, the active ingredient can be formulated with suitable polymeric or hydrophobic materials (for example as an emulsion in an acceptable oil) or ion exchange resins, or as sparingly soluble derivatives, for example, as a sparingly soluble salt.

A pharmaceutical composition or medicament of the present invention comprises (i) an effective amount of a compound as described herein that increases the level or activity of ZNF545 protein, and (ii) another therapeutic agent. When used with a compound of the present invention, such therapeutic agent may be used individually, sequentially, or in combination with one or more other such therapeutic agents (e.g., a first therapeutic agent, a second therapeutic agent, and a compound of the present invention). Administration may be by the same or different route of administration or together in the same pharmaceutical formulation.

3. Dosage

Pharmaceutical compositions or medicaments can be administered to a subject at a therapeutically effective dose to prevent, treat, or control gastric cancer as described herein. The pharmaceutical composition or medicament is administered to a subject in an amount sufficient to elicit an effective therapeutic response in the subject.

The dosage of active agents administered is dependent on the subject's body weight, age, individual condition, surface area or volume of the area to be treated and on the form of administration. The size of the dose also will be determined by the existence, nature, and extent of any adverse effects that accompany the administration of a particular compound in a particular subject. For example, each type of ZNF545 protein or nucleic acid encoding a ZNF545 protein will likely have a unique dosage. A unit dosage for oral administration to a mammal of about 50 to 70 kg may contain between about 5 and 500 mg of the active ingredient. Typically, a dosage of the active compounds of the present invention, is a dosage that is sufficient to achieve the desired effect. Optimal dosing schedules can be calculated from measurements of agent accumulation in the body of a subject. In general, dosage may be given once or more daily, weekly, or monthly. Persons of ordinary skill in the art can easily determine optimum dosages, dosing methodologies and repetition rates.

To achieve the desired therapeutic effect, compounds or agents may be administered for multiple days at the therapeutically effective daily dose. Thus, therapeutically effective administration of compounds to treat a pertinent condition or disease described herein in a subject requires periodic (e.g., daily) administration that continues for a period ranging from three days to two weeks or longer. Typically, agents will be administered for at least three consecutive days, often for at least five consecutive days, more often for at least ten, and sometimes for 20, 30, 40 or more consecutive days. While consecutive daily doses are a preferred route to achieve a therapeutically effective dose, a therapeutically beneficial effect can be achieved even if the agents are not administered daily, so long as the administration is repeated frequently enough to maintain a therapeutically effective concentration of the agents in the subject. For example, one can administer the agents every other day, every third day, or, if higher dose ranges are employed and tolerated by the subject, once a week.

Optimum dosages, toxicity, and therapeutic efficacy of such compounds or agents may vary depending on the relative potency of individual compounds or agents and can be determined by standard pharmaceutical procedures in cell cultures or experimental animals, for example, by determining the $LD_{50}$ (the dose lethal to 50% of the population) and the $ED_{50}$ (the dose therapeutically effective in 50% of the population). The dose ratio between toxic and therapeutic effects is the therapeutic index and can be expressed as the ratio, $LD_{50}/ED_{50}$. Agents that exhibit large therapeutic indices are preferred. While agents that exhibit toxic side effects can be used, care should be taken to design a delivery system that targets such agents to the site of affected tissue to minimize potential damage to normal cells and, thereby, reduce side effects.

The data obtained from, for example, cell culture assays and animal studies can be used to formulate a dosage range for use in humans. The dosage of such compounds lies preferably within a range of circulating concentrations that include the $ED_{50}$ with little or no toxicity. The dosage can vary within this range depending upon the dosage form employed and the route of administration. For any agents used in the methods of the invention, the therapeutically effective dose can be estimated initially from cell culture assays. A dose can be formulated in animal models to achieve a circulating plasma concentration range that includes the $IC_{50}$ (the concentration of the agent that achieves a half-maximal inhibition of symptoms) as determined in cell culture. Such information can be used to more accurately determine useful doses in humans. Levels in plasma can be measured, for example, by high performance liquid chromatography (HPLC). In general, the dose equivalent of agents is from about 1 ng/kg to 100 mg/kg for a typical subject.

Exemplary dosages for ZNF545 protein or a nucleic acid encoding a ZNF545 protein described herein are provided. Dosage for a ZNF545-encoding nucleic acid, such as an expression cassetter, can be between 0.1-0.5 mg/eye, with intravitreous administration (e.g., 5-30 mg/kg). Small organic compounds activators can be administered orally at between 5-1000 mg, or by intravenous infusion at between 10-500 mg/ml. Monoclonal antibody activators can be administered by intravenous injection or infusion at 50-500 mg/ml (over 120 minutes); 1-500 mg/kg (over 60 minutes); or 1-100 mg/kg (bolus) five times weekly. ZNF545 protein or peptide activators can be administered subcutaneously at 10-500 mg; 0.1-500 mg/kg intravenously twice daily, or about 50 mg once weekly, or 25 mg twice weekly.

Pharmaceutical compositions of the present invention can be administered alone or in combination with at least one additional therapeutic compound. Exemplary advantageous therapeutic compounds include systemic and topical anti-inflammatories, pain relievers, anti-histamines, anesthetic compounds, and the like. The additional therapeutic compound can be administered at the same time as, or even in the same composition with, main active ingredient (e.g., a ZNF545 protein or a nucleic acid encoding the protein). The additional therapeutic compound can also be administered separately, in a separate composition, or a different dosage form from the main active ingredient. Some doses of the main ingredient, such as a ZNF545 protein or a nucleic acid encoding a ZNF545 protein, can be administered at the same time as the additional therapeutic compound, while others are administered separately, depending on the particular symptoms and characteristics of the individual.

The dosage of a pharmaceutical composition of the invention can be adjusted throughout treatment, depending on severity of symptoms, frequency of recurrence, and physiological response to the therapeutic regimen. Those of skill in the art commonly engage in such adjustments in therapeutic regimen.

VII. Kits and Devices

The invention provides compositions and kits for practicing the methods described herein to assess the level of ZNF545 mRNA or ZNF545 protein in a subject, which can be used for various purposes such as detecting or diagnosing the presence of gastric cancer, determining the risk of developing gastric cancer, and monitoring the progression of gastric cancer in a patient.

Kits for carrying out assays for determining ZNF545 mRNA level typically include at least one oligonucleotide useful for specific hybridization with at least one segment of the ZNF545 coding sequence or its complementary sequence. Optionally, this oligonucleotide is labeled with a detectable moiety. In some cases, the kits may include at least two oligonucleotide primers that can be used in the amplification of at least one segment of ZNF545 DNA or mRNA by PCR, particularly by RT-PCR.

Kits for carrying out assays for determining ZNF545 protein level typically include at least one antibody useful for specific binding to the ZNF545 protein amino acid sequence. Optionally, this antibody is labeled with a detectable moiety. The antibody can be either a monoclonal antibody or a polyclonal antibody. In some cases, the kits may include at least two different antibodies, one for specific binding to the ZNF545 protein (i.e., the primary antibody) and the other for detection of the primary antibody (i.e., the secondary antibody), which is often attached to a detectable moiety.

Typically, the kits also include an appropriate standard control. The standard controls indicate the average value of ZNF545 protein or ZNF545 mRNA in the stomach epithelium of healthy subjects not suffering from gastric cancer. In some cases such standard control may be provided in the form of a set value. In addition, the kits of this invention may provide instruction manuals to guide users in analyzing test samples and assessing the presence, risk, or state of gastric cancer in a test subject.

In a further aspect, the present invention can also be embodied in a device or a system comprising one or more such devices, which is capable of carrying out all or some of the method steps described herein. For instance, in some cases, the device or system performs the following steps upon receiving a stomach tissue sample, e.g., a stomach mucosa sample taken from a subject being tested for detecting gastric cancer, assessing the risk of developing gastric cancer, or monitored for progression of the condition: (a) determining in sample the amount or concentration of ZNF545 mRNA, ZNF545 protein; (b) comparing the amount or concentration with a standard control value; and (c) providing an output indicating whether gastric cancer is present in the subject or whether the subject is at risk of developing gastric cancer, or whether there is a change, i.e., worsening or improvement, in the subject's gastric cancer condition. In other cases, the device or system of the invention performs the task of steps (b) and (c), after step (a) has been performed and the amount or concentration from (a) has been entered into the device. Preferably, the device or system is partially or fully automated.

EXAMPLES

The following examples are provided by way of illustration only and not by way of limitation. Those of skill in the art will readily recognize a variety of non-critical parameters that could be changed or modified to yield essentially the same or similar results.

The ZNF545 gene is located on chromosome 19q13.12 and produces a protein that is a member of the Kruppel-associated box-containing zinc finger proteins. It is localized to the nucleus and acts as a sequence-specific transcriptional repressor. In this study, it was determined that ZNF545 is commonly silenced or downregulated in gastric cancer by promoter methylation. ZNF545 acts as a novel tumor suppressor in gastric cancer. The anti-tumorigenic function of ZNF545 was modulated by inhibiting rRNA transcription by direct binding to rDNA promoter, inducing histone modification changes, and recruiting the corepressor, heterochromatin protein 1β. ZNF545 methylation is an epigenetic biomarker for diagnosing a patient with gastric cancer and/or predicting outcome (e.g., prognosis) in such a patient.

Gastric cancer is one of the most common malignancies and remains the second leading cause of cancer-related death worldwide. Although the mechanism leading to gastric cancer development remains elusive, epigenetic inactivation of tumour-related genes by promoter hypermethylation has been demonstrated to play an important role in the development of this malignancy. The identification of novel genes targeted by promoter methylation may help us to unravel the molecular mechanisms involved in inactivation of tumour suppressive pathways and pathogenesis of gastric cancer and to find better approaches to diagnostic and therapeutic evaluation. Kruppel-associated box domain-zinc-finger proteins (KRAB-ZFPs) constitute a large subfamily of zinc-finger proteins, which has become the largest family of transcriptional regulators in the human genome (Urrutia R., *Genome Biol.*, 2003, 4:231). KRAB-ZFP family members have been found to mediate transcriptional repression of RNA polymerases and binding and splicing of ribosomal RNAs (rRNAs) (Urrutia, supra). They can also mediate transcription silencing by binding to the promoter of target genes through a C2H2 zinc-finger domain and recruiting corepressors such as heterochromatin protein 1 (HP1) through the KRAB domain (Urrutia, supra; Zeng et al., *Epigenetics,* 2010, 5:284-92). Aberrant inactivation of KRAB-ZFPs has been reported to contribute to irregular gene expression and tumour development (Cheng et al., *Cancer Res.,* 2010, 70:6516-26). Characterization of the functional significance of KRAB-ZFP family members in gastric cancer may provide new insights for understanding the molecular mechanisms of gastric carcinogenesis and identifying potential targets for the diagnosis and treatment of gastric cancer. Through genome-wide screening, a novel KRAB-ZFP member, zinc-finger protein 545 (ZNF545), was identified and it was determined that it is methylated in gastric cancer.

The biological function of ZNF545 was determined by cell growth and apoptosis assays. The ZNF545 target signal pathway was identified by promoter luciferase assay, northern blot, run-on transcription assay, chromatin immunoprecipitation and coimmunoprecipitation assays. The clinical application of ZNF545 was assessed in primary gastric cancers. ZNF545 was silenced or reduced in 16 out of 18 gastric cancer cell lines by promoter hypermethylation. Restoration of ZNF545 expression in gastric cancer cell lines suppressed cell proliferation and induced apoptosis. These effects of ZNF545 were attributed to inhibition of ribosomal RNA (rRNA) transcription Inhibition of rRNA transcription by ZNF545 was further revealed to be associated with direct ribosomal DNA (rDNA) promoter binding, recruitment of the corepressor, heterochromatin protein 1β, and reduction of trimethylated histone H3 at the Lys4 residue at the rDNA locus. ZNF545 methylation was detected in 51.9% (41/79) of gastric cancer tissues. 27.0% (20/74) of adjacent non-tumour gastric tissues (p=0.001), but in none of 20 normal controls. Multivariate analysis revealed that patients with ZNF545 methylation had a significant decrease in overall survival. Kaplan-Meier survival curves showed that ZNF545 methylation was significantly associated with shortened survival in patients with stage 1-11 gastric cancer. ZNF545 acts as a functional tumour suppressor in gastric cancer by inhibiting rRNA transcription. Its methylation at early stages of gastric carcinogenesis is an independent prognostic factor.

Materials and Methods

Cell lines: Eighteen gastric cancer cell lines (AGS, Kato III, MKN28, MKN45, N87, SNU1, SNU16, YCC1, YCC2, YCC3, YCC6, YCC7, YCC9, YCC10, YCC11, YCC16, BGC823 and MGC803) and one normal gastric epithelial cell line (GES1) were used in this study. Cell lines were maintained in RPMI 1640 or Dulbecco's modified Eagle's medium (Gibco BRL, Rockville, Md., USA) with 10% fetal bovine serum. Human normal adult tissue RNA samples were purchased commercially (Stratagene, La Jolla, Calif., USA).

Gastric tissue samples: Paired gastric biopsy samples from primary tumour and adjacent non-tumour sites were obtained from patients with gastric cancer during endoscopy before any therapeutic intervention as described in, e.g., Yu et al., *Gastroenterology,* 2009, 136:640-54). The adjacent non-tumour area was subsequently verified by histology to be free of tumour infiltration. A total of 79 patients with confirmed gastric cancer and adjacent non-tumour tissues were examined for ZNF545 methylation. Adjacent non-tumour tissue was examined for diagnosis of chronic gastritis, glandular atrophy, intestinal metaplasia, and dysplasia of mucosa as stipulated by the updated Sydney system. The adjacent non-tumour tissues contained 45 samples with chronic gastritis and 34 samples with precancerous lesions (four with atrophy, 28 with intestinal metaplasia, and two with dysplasia). In addition, 20 age-matched subjects with normal upper gastroscopy were recruited as controls. The study protocol was approved by the Clinical Research Ethics Committee of the Chinese University of Hong Kong.

Assay of colony formation: Gastric cancer cells (AGS and MGC803) were transfected with pcDNA3.1-Flag-ZNF545 or empty pcDNA3.1. After 48 h of transfection, cells were selected with G418 (Calbiochem, Darmstadt, Germany) for 10-14 days. Colonies (≥50 cells/colony) were counted after being fixed with 70% ethanol and stained with 5% crystal violet.

Assay of cell viability: Cell viability was determined by the 3-(4,5-dimethylthiazol-2-yl)-5-(3-carboxymethoxyphenyl)-2-(4-sulfophenyl)-2H-tetrazolium assay (Promega, Madison, Wis., USA).

DDAO-SE labelling assay: CellTrace Far Red DDAO-SE dye (Invitrogen, Carlsbad, Calif., USA) was used as a live cell labelling dye to analyse cell proliferation. Equal numbers of stable ZNF545-expressing cells and control cells were seeded on a six-well plate. After 24 h, cells were incubated with 5 µM DDAO-SE for 10 min at 37° C. Staining was quenched by placing the cells in fresh culture medium and incubating for an additional 30 min at 37° C. Cells were then harvested at the starting time point and at 48 h, and the fluorescence intensity of the DDAO-SE signal, which corresponded to the proliferation status of the cultured cells, was measured by flow cytometry (Becton Dickinson Biosciences, Bedford, Mass., USA).

DDAO-SE labelling assay: CellTrace Far Red DDAO-SE dye (Invitrogen, Carlsbad, Calif., USA) was used as a live cell labelling dye to analyse cell proliferation. Equal numbers of stable ZNF545-expressing cells and control cells were seeded on a six-well plate. After 24 h, cells were incubated with 5 µM DDAO-SE for 10 min at 37° C. Staining was quenched by placing the cells in fresh culture medium and incubating for an additional 30 min at 37° C. Cells were then harvested at the starting time point and at 48 h, and the fluorescence intensity of the DDAO-SE signal, which corresponded to the proliferation status of the cultured cells, was measured by flow cytometry (Becton Dickinson Biosciences, Bedford, Mass., USA).

Assay of apoptosis: Apoptosis was determined by dual staining with annexin V-APC (Becton Dickinson Biosciences) and 7-aminoactinomycin (7-AAD) (Becton Dickinson Biosciences). Stable ZNF545-expressing or control cells (AGS and MGC803) were harvested, stained and analysed by flow cytometry according to the manufacturer's instructions (Becton Dickinson Biosciences). Sample fluorescence of 10000 cells was analysed using the FACSCalibur System (Becton Dickinson Pharmingen, San Jose, Calif., USA). The relative proportion of annexin V-positive and 7-AAD-negative cells was determined using ModFitLT software (Becton Dickinson Pharmingen) and counted as early apoptotic cells. All the experiments were performed in triplicate independently.

Fluorescent immunohistochemistry: AGS or MGC803 cells were seeded on coverslips on a six-well plate and transfected with pcDNA3.1-Flag-ZNF545. At 48 h after transfection, cells were fixed with 4% paraformaldehyde and permeabilised with 0.3% Triton X-100, blocked in 3% bovine serum albumin, and stained with monoclonal antibody to Flag M2 (1:50 dilution, F1804; Sigma, St Louis, Mo., USA) overnight at 4° C. After incubation with Texas Red-conjugated goat anti-rabbit IgG (1:500 dilution, Santa Cruz Biotechnology, Santa Cruz, Calif., USA), cells were mounted with mounting medium containing 4',6-diamidino-2-phenylindole (DAPI; Vector Laboratories, Burlingame, Calif., USA). Images were captured by fluorescent microscopy.

Dual-luciferase reporter assay: To assess the effect of rRNA promoter activity by ZNF545, gastric cancer cells (AGS, MGC803) were plated on a 24-well plate and cotransfected with the human polymerase I (Pol I) luciferase reporter plasmid, pHrD-IRES-Luc, and pRL-CMV vector with pcDNA3.1-Flag-ZNF545 or pc-DNA3.1. Cells were harvested 24 h after transfection, and luciferase activities were analysed by the dual-luciferase reporter assay system (Promega). Reporter activity was normalised to the control Renilla luciferase. Experiments were performed in triplicate.

Pre-rRNA analysis by Northern blot: For assay of ZNF545 overexpression, RNA was obtained from stable ZNF545-expressing MGC803 cells or control MGC803 cells. For ZNF545 knockdown assay, GES1 cells were transfected with ZNF545 small interfering RNA (siRNA) (sense, 5'-CCGUG-GUUAUCAUCUUAUUdT dT-3' (SEQ ID NO: 18); antisense, 3'-dTdTGGCACCAAUAGUAGAAUAA-5' (SEQ ID NO:19)) (RiboBio, Guangzhou, China) or negative control siRNA (RiboBio) and harvested after 24 h of transfection for RNA extractions. Total RNA was isolated with TRizol Reagent (Invitrogen, Carlsbad, Calif.). A pre-rRNA DNA probe was generated by amplifying human ribosomal DNA (rDNA) sequences from −65 to +438 using the forward primer 5'-CCCGGGGGAGGTATATCTTT-3' (SEQ ID NO:20) and the reverse primer 5'-GACGTCACCACATC-GATCAC-3' (SEQ ID NO:21), and then gel-purified and random prime labelled with digoxigenin-11-dUTP using the DIG High Prime DNA Labelling and Detection Starter Kit II (Roche Applied Science, Indianapolis, Ind., USA). Northern blots were performed by electrophoresis of 25 µg RNA samples in standard formaldehyde-agarose gels followed by transfer to Hybond-N+ membranes (Amersham/GE Healthcare Biosciences, Pittsburgh, Pa., USA) and UV cross-linking Membranes were hybridized with the digoxigenin-labelled probe and detected according to the manufacturer's instructions (Roche Applied Science). Ethidium bromide staining of 28S was used as loading control.

Run-on transcription assay Run-on transcription assay: For immunodetection of nascent rRNA, pulses of 5-fluorouridine (5-FU) (F5130; Sigma) were administered as described in, e.g., Torrano et al., *J. Cell Sci.*, 2006, 119:1746-59. ZNF545-expressing MGC803 cells or control MGC803 cells were seeded on coverslips on a six-well plate. Pulses of 5-FU were performed by adding 5-FU to a final concentration of 2 mM in the culture medium. After 10 min, cells were fixed with 3.7% paraformaldehyde for 5 min. The incorporation of 5-FU into nascent RNA was detected with an antibody against halogenated UTP (1:50, anti-bromodeoxyuridine (BrdU) clone BU-33, B8434; Sigma) and a Texas Red-conjugated secondary antibody.

HP1β knockdown assay: MGC803 cells were cotransfected with 50 nM HP1βsiRNA (sense, 5'-GGAAGGGAUU-CUCAGAUGAdTdT-3' (SEQ ID NO:22); antisense, 3'-dT-dTCCUUCCCUAAGAGUCUACU-5' (SEQ ID NO:23)) (RiboBio) or control siRNA (RiboBio) and expression vector pcDNA3.1+ or pcDNA3.1-Flag-ZNF545 using lipofectamine 2000 (Invitrogen) according to the manufacturer's protocols. At 48 h after transfection, cells were harvested and cross-linked for the chromatin immunoprecipitation (ChiP) assay.

Chromatin immunoprecipitation: ChiP experiments were performed as described in, e.g., Lee et al., *Nat. Protoc.*, 2006, 1:729-48. Briefly, stable ZNF545-expressing MGC803 cells and control cells were cross-linked with formaldehyde for 10 min at room temperature. The cross-linking reaction was stopped by the addition of glycine, and the cells were collected for nuclear protein extraction. Chromatin from extracted cross-linked nuclei was sheared by sonication and precipitated with antibodies to Flag (F1804; Sigma-Aldrich) or trimethylated histone H3 at the Lys4 residue (H3K4me3; 07-043; Milipore, Billerica, Mass., USA); immunoprecipitated protein-DNA complex was then captured with protein-G magnetic beads. Equal numbers of cells ((1-2)×10$^7$) were used for each immunoprecipitation. The same amount of non-specific IgG was used as control. After reversal of the cross-link and digestion of proteins with proteinase K, the immunoprecipitated DNA was isolated by the phenol/chloroform/isoamyl alcohol method. Levels of human rDNA were examined by real-time PCR with primer sequences from −65 to +33 (forward, 5'-CCCGGGGGAGGTATATCTTT-3' (SEQ ID NO: 24); reverse, 5'-CCAACCTCTCCGACGACA-3' (SEQ ID NO: 25)). Fold enrichment was calculated relative to the background detected with nonspecific IgG using the following formula: fold enrichment=$2^{(CT of IgG - CT of antibody)}$. The CT (cycle threshold) is defined as the number of cycles required for the fluorescent signal to cross the threshold in a real-time PCR assay. The experiment was repeated three times independently.

Coimmunoprecipitation: MGC803 cells were cotransfected with pcDNA3.1-Flag-ZNF545 and pEGFP-C1-HP1β (green fluorescent protein (GFP)-tagged mouse HP1β). After 48 h of transfection, total protein was extracted in RIPA buffer (5% sodium deoxycholate, 0.1% SDS, 10 mM Na$_3$VO4, 50 mM NaF, 1% Nonidet P40, phosphate buffered saline buffer, 1× protease inhibitor mixture) for 1 h on ice. Cell lysates were centrifuged and the pellet was discarded. Protein lysates were precleared by incubation with 20 µl protein G-agarose at 4° C. for 1 h. After a brief centrifugation, the supernatant was transferred to a new tube. Each immunoprecipitation reaction was performed with 300 µg precleared cell lysate, 2 µg antibody against Flag, and 50 µl protein G slurry for overnight incubation at 4° C. The supernatant was removed, and the protein G beads were washed in lysis buffer. Finally, immunoprecipitated protein complex was added with 2× loading buffer and boiled to denature the protein and separate it from protein G beads. The precipitated proteins were evaluated by Western blot using primary antibody against GFP (Abcam, Cambridge, Mass., USA).

Statistical analysis: Data are presented as mean±SD. The independent Student's t-test was used to compare the difference between two preselected groups. Relationships between ZNF545 methylation and clinicopathological characteristics of patients with gastric cancer were compared using Pearson's $\chi^2$ test. Univariate and multivariate Cox regression analysis was performed to assess the prognostic value of ZNF545 methylation. Overall survival in relation to methylation status was evaluated from Kaplan-Meier survival curves and the log-rank test. $p<0.05$ was taken as statistical significance.

Western blot: Total protein was extracted from cell pellet. Thirty micrograms of protein from each sample were separated on 12% SDS-PAGE and transferred onto nitrocellulose membranes (GE Healthcare, Piscataway, N.J.). Blots were immunostained with primary antibody, and then secondary antibody. GAPDH served as a gel loading control.

Methylation-specific PCR and bisulfite genomic sequencing: DNA bisulfite treatment, methylation-specific PCR (MSP), and bisulfite genomic sequencing (BGS) were performed as described in, e.g., Yu, supra). The bisulfite-modified DNA was amplified by using primer pairs that specifically amplify either methylated or unmethylated sequences of the ZNF545 gene (see FIG. 8). Amplified BGS products for ZNF545 promoter were sequenced (FIG. 1A).

Demethylation treatment with 5-Aza-2'-Deoxycytidine: Gastric cancer cells (1×10$^5$/mL) were seeded. After 24 hours, cells were treated with 2 µmol/L of the DNA demethylating agent 5-Aza-2'-deoxycytidine (5-Aza) (Sigma-Aldrich, St. Louis, Mo.) for 96 hours. Cells then were harvested for RNA extraction.

Construction of ZNF545 expression plasmid: The full-length ZNF545 cDNA was amplified and cloned into the pCDNA3.1+ expression vector (Invitrogen, Carlsbad, Calif.). pBABE-puro-Flag-ZNF545 was generated by inserting the cloned full-length ZNF545 into pBABE-puro empty vector (Addgene, Cambridge, Mass.).

Establishment of stable ZNF545 expressing cells: 293FT cells (Invitrogen) were co-transfected with pBABE-puro-Flag-ZNF545 or pBABE-puro empty vector, two packaging plasmids pUMVC (Addgene) and pCMV-VSV-G (Addgene) at the ratio of 1:0.9:0.1 to produce retroviruses pBABE-puro-ZNF545 or pBABE-puro control. After 48 hour post-transfection, the supernatant containing retrovirus pBABE-puro-Flag-ZNF545 or pBABE-puro control was harvested and added to AGS or MGC803 cells. After 24 hour transduction, the media containing retrovirus was removed and infected cells were selected for 5-7 days with 0.5 µg/ml antibiotic puromycin (Invitrogen) to establish stable ZNF545 transfection.

Results

1. Silence or Downregulation of ZNF545 by Promoter Methylation of ZNF545 in Gastric Cancer ZNF545 was expressed in normal human gastric tissue and the normal human gastric epithelial cell line (GES1) (FIG. 1B). In the 18 gastric cancer cell lines examined, mRNA expression of ZNF545 was silenced in 14, reduced in 2, and detected in YCC10 and BGC823 cell lines (FIG. 1B). To examine the contribution of promoter methylation to the downregulation of ZNF545, its methylation status was examined by methylation-specific PCR (MSP). Promoter methylation was observed in all 16 silenced or downregulated gastric cancer cell lines, but no methylation was observed in BGC823 and slight methylation in YCC10, both of which exhibit ZNF545 expression (FIG. 1B). The normal gastric epithelial cell line, GES1, showed ZNF545 expression, but no promoter methylation. The ZNF545 methylation status was confirmed by bisulfite genome sequencing (BGS). The BGS results were consistent with those of MSP, in which dense methylation was found in methylated cell lines (AGS, MKN45 and Katoiii), but not in the unmethylated BGC823 and GES1 cell lines and normal gastric tissues (FIG. 1C). To test whether methylation directly mediates ZNF545 silencing, four silenced cell lines (MKN28, AGS, Katoiii and SNU1) were treated with the demethylation agent, 5-Aza-2'deoxycytidine (5-Aza; Sigma-Aldrich). This treatment restored ZNF545 expression in all the silenced cell lines (FIG. 1D), indicating that the transcriptional silence of ZNF545 was mediated by promoter methylation in gastric cancer cells.

2. ZNF545 Inhibits Gastric Cancer Cell Growth

Figure 2:
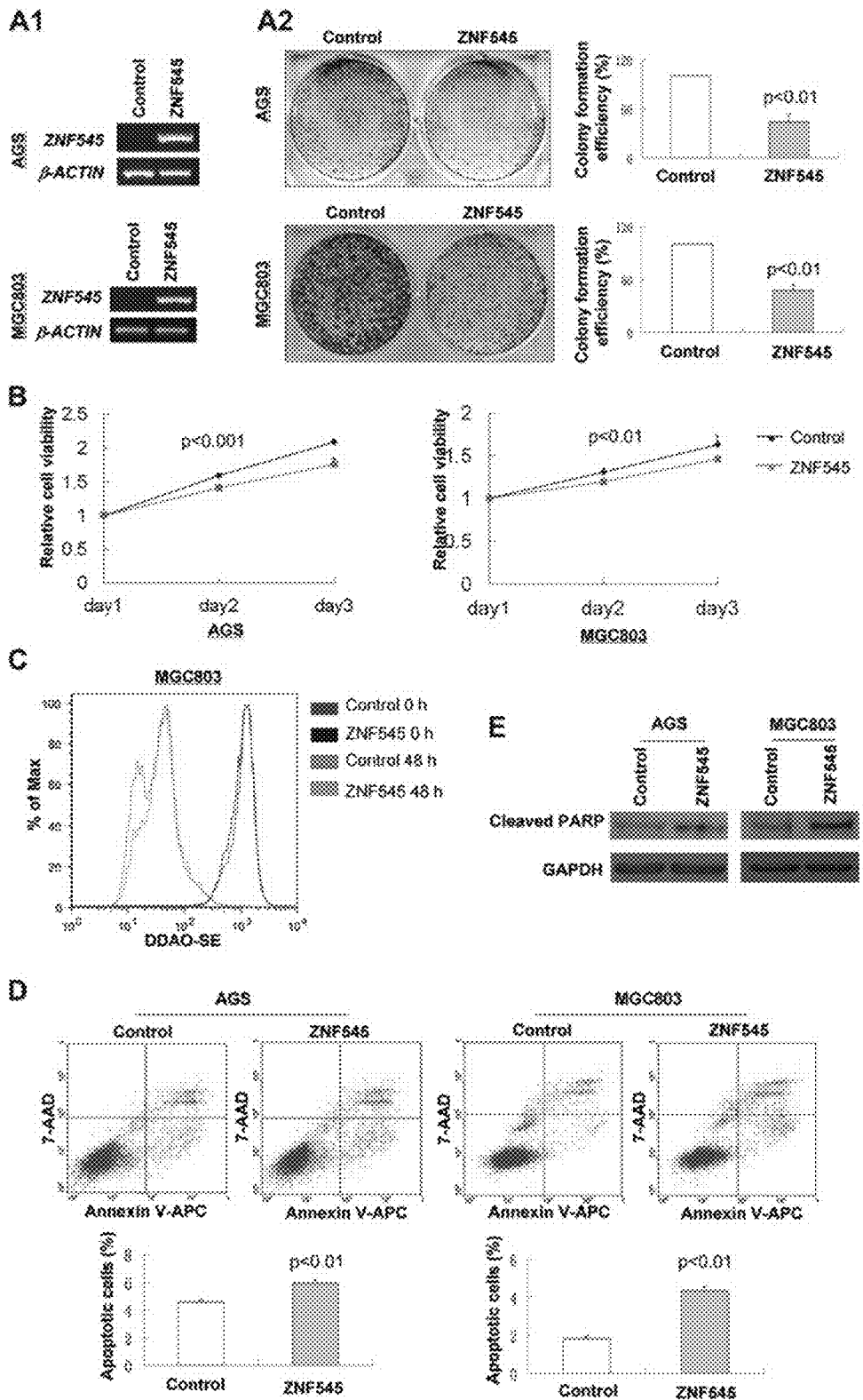
FIG. 2. ZNF545 inhibited tumour cell clonogenicity and induced apoptosis of gastric cancer cells. (A) Effect of ZNF545 overexpression (A1) on colony formation in AGS and MGC803 cells (A2). (B) Effect of ZNF545 on cell viability was evaluated by 3-(4,5-dimethylthiazol-2-yl)-5-(3-carboxymethoxyphenyl)-2-(4-sulfophenyl)-2H-tetrazolium assay in AGS and MGC803 cells. (C) Effect of ZNF545 on MGC803 cell proliferation by DDAO-SE assay. The fluorescence intensities of ZNF545-expressing cells and control cells at 0 h and 48 h were evaluated by flow cytometry after staining with DDAO-SE dye. (D) Cell apoptosis was examined by flow cytometry analysis of annexin V-APC and 7-aminoactinomycin (7-AAD) double staining. (E) Protein expression of cleaved poly(ADP-ribose) polymerase (PARP) was evaluated by western blot.

To elucidate the function of ZNF545 in gastric cancer, the effect of ZNF545 re-expression on growth characteristics of gastric cancer cells was examined by colony formation assay. A ZNF545-expression plasmid was stably transfected into cancer cells lacking endogenous ZNF545 expression, such as AGS and MGC803 cells (FIG. 2A). Re-expression of ZNF545 was confirmed by PCR analysis (FIG. 2A1). The colonies formed in ZNF545-transfected AGS and MGC803 cells were significantly fewer than in control vector transfected cells (p<0.001) (FIG. 2A2). In addition, ectopic expression of ZNF545 caused a significant decrease in cell proliferation in AGS (p<0.001) and MGC803 (p<0.01) cells (FIG. 2B). The inhibitory effect on cancer cell proliferation was further confirmed by the DDAO-SE labelling assay. At 48 h after DDAO-SE labeling, the fluorescence signal of ZNF545-expressing cells was higher than that of control cells, indicating that ZNF545-expressing cells divided more slowly with less loss of fluorescence signal (FIG. 2C).

3. ZNF545 Induces Cell Apoptosis

To examine the contribution of apoptosis to the observed suppression of growth by ZNF545, cell apoptosis was evaluated using double staining with annexin V-APC and 7-AAD. Ectopic expression of ZNF545 led to a significant increase in early apoptotic cells in both AGS (p<0.01) and MGC803 (p<0.01) cells compared with controls (FIG. 2D). In keeping with this finding, re-expression of ZNF545 significantly enhanced cleavage of poly(ADP-ribose) polymerase in stably transfected AGS and MGC803 cells compared with controls (FIG. 2E).

4. ZNF545 is Localised to the Nucleolus

To probe the function of ZNF545, its subcellular localization was examined in pcDNA3.1-Flag-ZNF545-transfected AGS and MGC803 cells using an antibody against Flag. Immunofluorescent staining showed that ZNF545 was localized to the nucleolus of both cell lines (FIG. 3A), which is the site of ribosome biogenesis (e.g., rRNA synthesis) and is surrounded by clusters of genes that encode rRNA (Pederseon T., Cold Spring Harb Perspect Biol., 2011, 3:pii: a000638).

5. ZNF545 Inhibits rRNA Transcription as a Transcriptional Repressor

Figure 3:
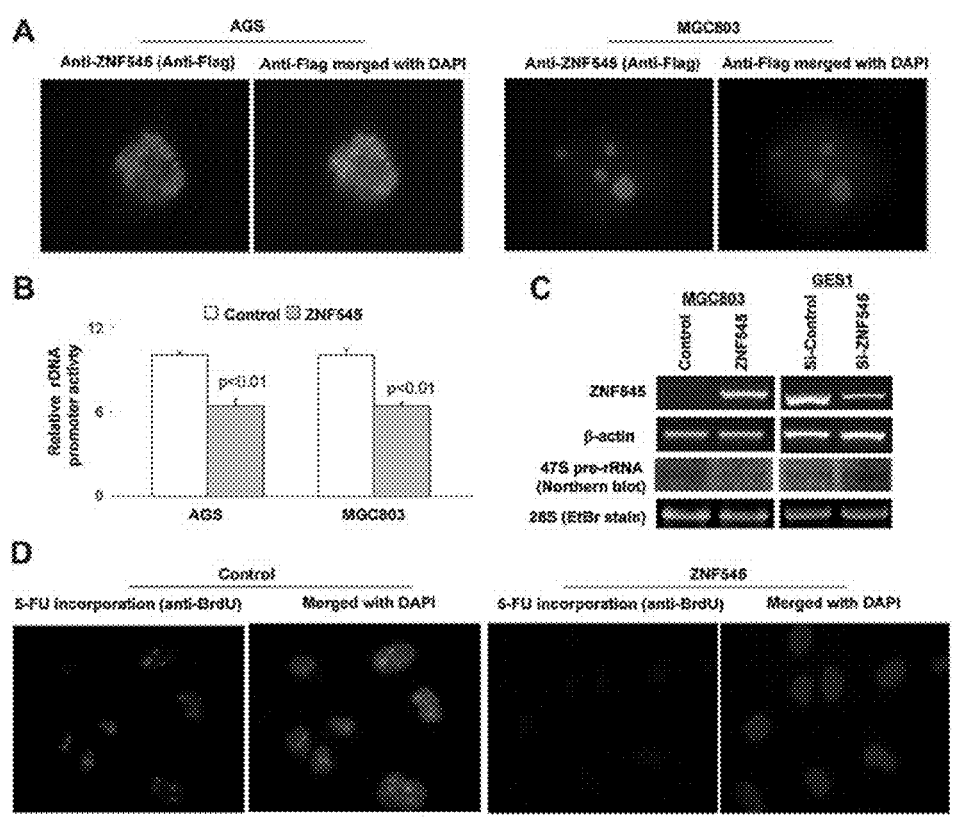
FIG. 3. ZNF545 inhibited rRNA transcription as a transcription repressor. (A) ZNF545 localized in the nucleolus by immunofluorescence. (B) Effect of ZNF545 on rDNA promoter activity was assessed by dual luciferase reporter assay. (C) Levels of pre-rRNA were analysed by northern blot in response to overexpression or siRNA-mediated depletion of ZNF545 in MGC803 cells. Ethidium bromide (EtBr) staining of 28S was used as loading control. (D) De novo synthesis of pre-rRNA was monitored by in situ 5-fluorouridine (5-FU) incorporation into nascent rRNA in ZNF545-expressing and control MGC803 cells. BrdU, bromodeoxyuridine; DAPI, 4',6-diamidino-2-phenylindole.

As a member of the KRAB-containing zinc-finger family, ZNF545 functions as a transcriptional repressor. (Urrita, supra). Furthermore, the results described herein shows that ZNF545 is localised to the nucleolus, where rRNA is transcribed. Dual-luciferase reporter assay was performed to assess the effect of rDNA promoter activity by ZNF545. Re-expression of ZNF545 suppressed transcription on the rDNA promoter reporter plasmid in both AGS (p<0.01) and MGC803 (p<0.01) cells (FIG. 3B). To further confirm that ZNF545 exerts a negative influence on RNA Pol I transcription, pre-rRNA synthesis was measured in response to overexpression or siRNA-mediated depletion of ZNF545 by Northern blot analysis. Pre-rRNA synthesis was greatly reduced in ZNF545-expressing MGC803 cells (FIG. 3C). In contrast, knockdown of ZNF545 by siRNA resulted in a clear increase in the expression of pre-rRNA, compared controls (FIG. 3C). In keeping with these findings, monitoring of de novo synthesis of pre-rRNA by 5-FU incorporation into nascent nucleolar RNA revealed that the active rRNA transcription sites, as indicated by foci of 5-FU incorporation signal, were notably decreased in ZNF545-expressing MGC803 cells, compared with controls (FIG. 3D). The data shows that ZNF545 acts as a transcription repressor and inhibits RNA transcription.

6. ZNF545 Directly Binds to rDNA Promoter Causing Demethylation of H3K4Me3

Figure 4:
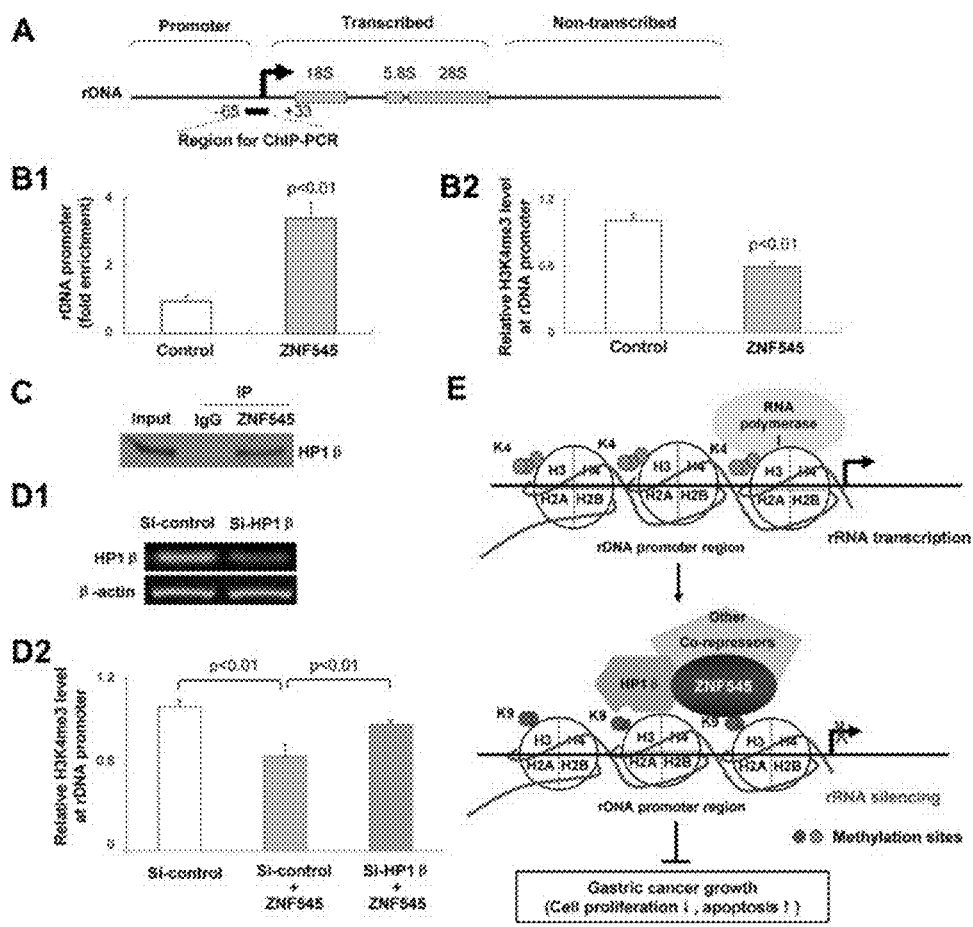
FIG. 4. rRNA silencing by ZNF545 was mediated by directly binding to rDNA promoter, recruitment of the corepressor, heterochromatin protein 1β (HP1β), and loss of trimethylated histone H3 at the lysine 4 residue (H3K4me3) at the rDNA promoter locus. (A) Schematic representation of a human rDNA repeat. The primer pair for chromatin immunoprecipitation (ChIP)-PCR and their approximate positions relative to the rRNA transcription start are indicated. (B1) Fold enrichment of Flag-ZNF545 occupancy at the rDNA promoter obtained with anti-Flag versus rabbit immunoglobulin was determined by quantitative ChIP-PCR analysis using chromatin prepared from Flag-ZNF545-expressing and control MGC803 cells. (B2) The relative fold enrichment of H3K4me3 at the rDNA promoter was determined by quantitative ChIP-PCR. (C) Coimmunoprecipitation showed the physical interaction between ZNF545 and HP1 β. (D) The relative fold enrichment of H3K4me3 at the rDNA promoter was examined on HP1 β knockdown (D1) by quantitative ChIP-PCR (D2). (E) Proposed mechanistic model of tumour suppression by ZNF545.

The presence of a C2H2-type zinc-finger DNA-binding domain in ZNF545 protein suggests that ZNF545 may bind to the rDNA promoter. To test this, the ZNF545-DNA complex was immunoprecipitated from Flag-ZNF545-expressing MGC803 cells using an antibody to Flag. Quantitative ChIP-PCR was performed with specific primers targeting the rDNA promoter from −65 to +33 relative to the transcription start site (FIG. 4A) (see, e.g., Grandori et al., Nat. Cell Biol., 2005, 7:311-18; Frescas et al., Nature, 2007, 450:309-13). The results of ChIP-PCR confirmed that ZNF545 was bound to the core rDNA promoter region with about threefold enrichment (FIG. 4B1). Regulation of rRNA transcription within the nucleolus is controlled by distinct epigenetic marks. Moreover, H3K4me3 is a critical epigenetic marker for active rRNA transcription (Santoro, R., Cell Mol. Life Sci., 2005, 62:2067-79; Bartova et al., J. Histochem. Cytochem., 2010, 58:391-403). The effect of ZNF545 overexpression on H3K4me3 levels in the rDNA promoter region was tested using quantitative ChIP-PCR. The results show that ZNF545 reduced the level of H3K4me3 on the core rDNA promoter region (FIG. 4B2).

7. ZNF545 Recruits the Corepressor, HP1β for rRNA Transcription Repression

Since the KRAB domain of KRAB-containing zinc-finger proteins serves as a scaffold for recruiting corepressors, such as HP1, to suppress RNA transcription, the protein interaction between ZNF545 and HP1 was examined by coimmunoprecipitation. The protein complex was coimmunoprecipitated using an antibody to Flag and extracts prepared from MGC803 cells cotransfected with pcDNA3.1-Flag-ZNF545 and pEGFR-C1-HP1β. HP1β was detected by Western blotting using antibody to GFP, indicating an association between ZNF545 and HP1β (FIG. 4C). Upon HP1β knockdown (FIG. 4D1), the H3K4me3 level on the rDNA promoter region was significantly restored in ZNF545-expressing cells compared with control siRNA-transfected ZNF545-expressing cells (FIG. 4D2). These results indicate that HP1β blockade (by knockdown) partially relieved ZNF545-mediated rRNA repression.

Figure 5:
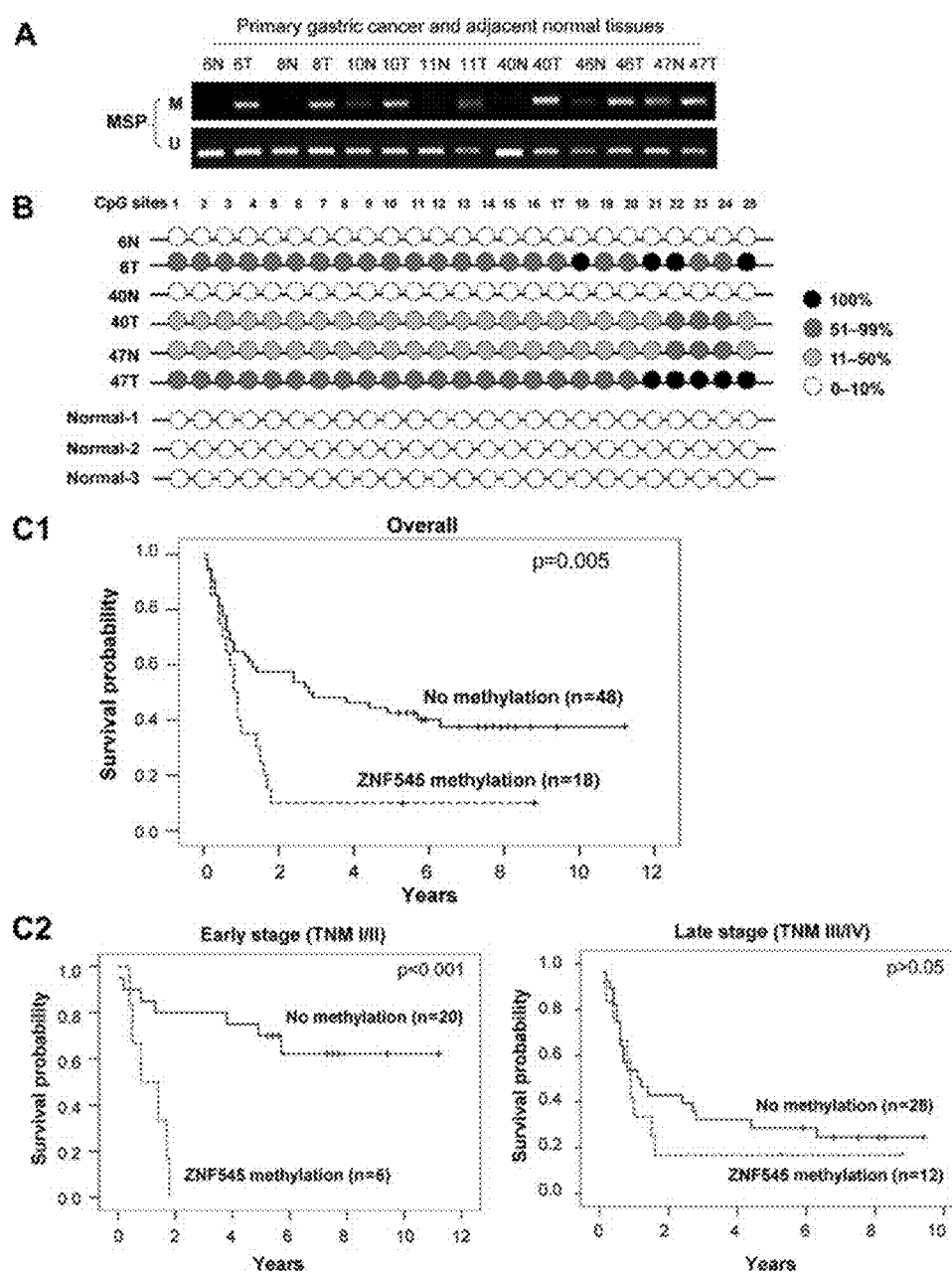
FIG. 5. ZNF545 is commonly methylated in primary gastric cancer. (A) Methylation-specific PCR (MSP) of ZNF545 promoter region in paired gastric cancers. M, methylated; U, unmethylated; N, normal; T, tumour. (B) Representative bisulfite genomic sequencing (BGS) result of ZNF545 methylation status in gastric cancer, adjacent non-tumour and normal gastric tissue samples. (C1) Kaplan-Meier survival curves show that patients with ZNF545 methylation in adjacent non-tumour tissues had poorer survival than others. (C2) Kaplan-Meier curves of patients with gastric cancer, stratified by ZNF545 methylation status, of early stage (tumour, node, metastases (TNM) I/II) and late stage (TNM III/IV).

8. Promoter Methylation of ZNF545 is Associated with Poor Survival of Patients with Gastric Cancer The clinical application of ZNF545 methylation was evaluated in 79 paired primary gastric cancers and in 20 healthy gastric tissue samples. Partial and dense promoter methylation of ZNF545 was detected in 51.9% (41/79) of cancer tissues and 27.0% (20/74) of adjacent non-tumour tissues (p=0.001), but none of the 20 normal gastric biopsy samples (FIG. 5A,B). There was no correlation between the methylation status of ZNF545 and clinicopathological features of patients with gastric cancer (FIGS. 9 and 10; Tables 4 and 5). Partial methylation at ZNF545 promoter was observed in most of the primary tumour samples. This is mainly because gastric tumour tissue also contains normal epithelial cells, stromal cells and/or infiltrating immune cells with an unmethylated part.

In univariate Cox regression analysis (FIG. 6), ZNF545 methylation in adjacent non-tumour tissues (the corresponding tumour tissues also methylated) was associated with a significantly increased risk of cancer-related death (RR 2.28; 95% CI 1.26 to 4.13; p<0.007). After adjustment for age, gender and tumour, node, metastases (TNM) stage, ZNF545 methylation in adjacent non-tumour tissues was found to predict poorer survival (RR 2.01; 95% CI 1.04 to 4.12; p=0.03) (FIG. 7). Kaplan-Meier survival curves showed that the overall survival of patients with gastric cancer who had ZNF545 methylation in adjacent non-tumour tissues was significantly shorter than that of other patients (p=0.005, log-rank test) (FIG. 5C1). After further stratification by TNM stage, patients with gastric cancer and ZNF545 methylation in adjacent non-tumour tissues had significantly shorter survival in stage I/II (p<0.001) (FIG. 5C2), but not in stage III/IV (FIG. 5C2).

Discussion

In this study, ZNF545 expression was silenced or reduced in 16 out of 18 gastric cancer cell lines. The downregulation was measured by MSP and BGS and was due to promoter methylation. Demethylation treatment restored ZNF545 expression in all silenced cell lines with full methylation of ZNF545, confirming that promoter methylation is a principal mechanism for transcriptional silencing of ZNF545 in gastric cancer. As downregulation of ZNF545 was observed in gastric cancer and not in normal gastric tissues, ZNF545 appears to function as a tumour suppressor. Ectopic expression of ZNF545 in silenced gastric cancer cell lines (AGS and MGC803) dramatically suppressed clonogenicity (FIG. 2A), inhibited cell proliferation (FIG. 2B,C) and induced apoptosis (FIG. 2D,E). Taken together, the data demonstrates that ZNF545 functions as a tumour suppressor in gastric cancer.

It was shown in gastric cancer cells that ZNF545 protein is localized to the nucleolus which is the site of rRNA synthesis. Further experimentation revealed that rDNA promoter activity was reduced by ZNF545 in both AGS and MGC803 cell lines (FIG. 3B). It was confirmed that ZNF545 inhibited pre-rRNA synthesis, as by Northern blot (FIG. 3C) and in situ immunodetection of BrdU incorporation into nascent rRNA (FIG. 3D). An enlarged nucleolus with increased rRNA transcription and ribosome biogenesis has been found to be characteristic for all tumour types, as cancer cells require robust synthesis of rRNA and ribosomes to meet the high demand for rapid cell division and proliferation by supporting protein synthesis (Bartova et al, supra; Drygin et al., *Annu Rev Pharmacol Toxicol*, 2010, 50:131-56; Derenzini et al., *Histopathology*, 2009, 54:753-6; Montanaro et al., *Am. J. Pathol.*, 2008, 173:301-10). In summary, the tumour-suppressive function of ZNF545 in gastric cancer is associated with the inhibition of rRNA transcription.

A recent study has indicated that the MYC oncogene binds directly to rDNA loci and activates rRNA transcription to promote tumorigenesis (van Riggelen et al., *Nat. Rev. Cancer*, 2010, 10:301-9). It has also been found, by isolating the RNA Pol I coactivator, UBF (upstream binding transcription factor, RNA polymerase I), from rDNA, that the tumour suppressor retinoblastoma protein (pRb) impairs RNA Pol I transcription complex formation, leading to reduced rRNA synthesis and inhibited cell growth (Drygin et al., supra). Moreover, perturbation of ribosome biogenesis can trigger cell apoptosis (Drygin et al., supra; Azuma et al., *J. Biol. Chem.*, 2006, 281: 13309-16; Yuan et al., *Mol. Cell*, 2005, 19:88-87; Huang et al., *Leuk. Res.*, 2008, 32:131-41; Kalita et al., *J. Neurochem.*, 2008, 105:2286-99; Deisenroth et al., *Oncogene*, 2010, 29:4253-60).

Inhibition of rRNA synthesis can halt the progression of ribosome assembly and lead to nucleolar stress/structure disruption and an excess of free ribosomal proteins (Yuan et al., supra; Huang et al, supra; Deisenroth et al., supra). In turn, ribosomal proteins such as L11 efflux into the nucleoplasm and bind to murine double minute 2 (MDM2), blocking MDM2-mediated p53 ubiquitination and degradation and inducing p53-mediated apoptosis (Huang et al, supra; Deisenroth et al., supra). It is therefore likely that the inhibitory properties of ZNF545 against gastric cancer cell growth observed in this study are to be explained, at least in part, by the induction of apoptosis-resultant suppression of rRNA transcription. Experiments were conducted to examine the molecular mechanisms by which ZNF545 exerts its suppressive effect on rRNA transcription in gastric cancer cell. Using quantitative ChiP-PCR it was determined that ZNF545 binds directly to the rDNA core promoter region in MGC803 cells. Moreover, ZNF545 reduced the level of H3K4me3, a transcriptionally active histone modification marker associated with relaxed chromatin structure and active transcription at the rDNA promoter (Best et al., *Drug Discov Today*, 2010, 15:65-70). These results indicate that ZNF545 promoted conversion of the transcriptionally active state of chromatin at the rDNA promoter into the repressive state, and thus ZNF545 can act as a transcriptional suppressor. In addition, ZNF545 recruits the corepressor, HP1β, as demonstrated by coimmunoprecipitation assay. HP1β knockdown partially relieved ZNF545-mediated inhibition of rRNA transcription, indicating that HP1β was an essential corepressor binding target for ZNF545 in regulating rRNA repression.

It has been reported that HP1 binds to the repressive chromatin marker, methylated H3K9, which contributes to chromatin condensation and maintenance of the close structure of heterochromatin (Bannister et al., *Nature*, 2001, 410:120-4; Maison et al., *Nat. Rev. Mol. Cell Biol.*, 2004, 5:396-304; Groner et al., *PLoS Genet.*, 2010, 6:e1000869) In agreement with the data described herein, KRABZFP binds specifically to a gene promoter through its multiple zinc fingers, whereas its KRAB domain recruits corepressors, including HP1, to form heterochromatin and silences gene expression (Groner et al., supra). Collectively, the findings indicate that ZNF545 binds directly to rDNA promoter and recruits the corepressor HP1β, leading to decreased chromatin in an active configuration at the rDNA promoter and ultimately rRNA silencing, thereby contributing to a tumour-suppressive effect (FIG. 4E).

To ascertain the clinical application of ZNF545 as a biomarker of gastric tumorigenesis, BGS promoter methylation of ZNF545 was evaluated in 79 paired primary gastric cancers and 20 normal controls. ZNF545 promoter methylation was observed in 51.9% of primary gastric tumours, and not in normal gastric tissues, suggesting that methylation-mediated ZNF545 inactivation is common to gastric carcinogenesis. In some cases (27.0%), ZNF545 methylation was observed in both the tumours and the adjacent non-tumour tissues, although the degree and frequency of methylation were distinctly higher in the tumours than in their corresponding non-tumour tissues. Notably, among the non-tumour tissues, ZNF545 methylation was detected in precancerous lesions and chronic gastritis (FIG. 10), suggesting that aberrant ZNF545 promoter hypermethylation occurred early in premalignant lesions of gastric mucosa and accumulated during the process of gastric carcinogenesis. Loss of ZNF545 expression by promoter methylation contributed to gastric cancer progression by facilitating cell aberrant growth and evading apoptosis. ZNF545 methylation detected in adjacent non-tumour tissues significantly predicted poorer survival in patients with early stage gastric cancer (FIG. 5C and FIG. 7). This is most likely attributed to the fact that adjacent, normal gastric tissues containing precancerous lesions were not removed by surgery, whereas precancerous lesions with ZNF545 methylation are more predisposed to malignant transformation and cancer development. Thus, ZNF545 methylation can be regarded as a valuable prognostic factor for patients with early stage gastric cancer.

In conclusion, the novel functional tumour suppressor gene, ZNF545, is inactivated by promoter methylation in gastric cancer. ZNF545 suppresses gastric cancer growth by silencing rRNA transcription through direct binding to the rDNA promoter, inducing histone modification changes and recruitment of the corepressor, HP1β. ZNF545 methylation detected in adjacent non-tumour tissues is associated with shorter survival in early stages of gastric cancers. Thus, ZNF545 methylation serves as a useful biomarker for the diagnosis and/or prognosis of early stage gastric cancer.

All publications, including patents, patent applications, and GenBank Accession Numbers, cited herein are hereby incorporated by reference in their entirety for all purposes.

INFORMAL SEQUENCE LISTING

```
SEQ ID NO: 1
Promoter region of human ZNF545 gene (MSP region)
TCCCCTCCAGGCCCTGCCGCGCCGTCCCCAGGCGCTAAGGGACTCGAAGCGCAGCCTCG
CTGGGACGGACCTAGCTCCGGCTCCGGGTTCACGCAGAGCAGGGGCTGCACCAGCGAGC
GGACCCTTGAGACTGGCCGCGCCTGCGCACTCCGTGAGCGCGCCCGGCCCTCCCAGCAG SEQ ID NO: 2
Promoter region of human ZNF545 gene (BGS region)
Sequence of promoter region of human ZNF545 gene (-271 to +157
from the transcription start site)
TCACAGGGCTCCCTAGTTGGCACTATAGAGAGGCGGTCGCGGGCGCCCCTCTTTAACGC
GCCAGCCATCTGTCCCCGCTCCCCTCCAGGCCCTGCCGCGCCGTCCCCAGGCGCTAAGG
GACTCGAAGCGCAGCCTCGCTGGGACGGACCTAGCTCCGGCTCCGGGTTCACGCAGAGC
AGGGGCTGCACCAGCGAGCGGACCCTTGAGACTGGCCGCGCCTGCGCACTCCGTGAGCG
CGCCCGGCCCTCCCAGCAGCCTCCGCGCGCAGCCCGTTAGGCCCCGGGGATTGTGGCGT
GACCCGGCAGCGGCTTCCTCCGTTCGGGCATCGCTGTGCCTCGGGTTCGCGCCCCGAGT
GAGCAGTCCTGGCCCGGAGCGTCGGTCCTGGTAATCTGTAGGAAAAGCGCTGCGGCCCA
GGGGGTAAAGAGAGG SEQ ID NO: 3
Human ZNF545 cDNA coding sequence(CDS)(1596 bp)
ATGGCCCTTCGATCAGTGATGTTCAGTGATGTATCCATAGACTTCTCTCCAGAAGAGTGGGAATA
CCTGGACTTGGAACAAAAGGACTTGTACAGAGATGTCATGTTGGAGAACTACAGCAACTTGGTCT
CACTGGGATGCTTCATTTCTAAACCAGATGTGATTTCCTCATTGGAGCAAGGAAAAGAGCCTTGG
AAAGTTGTGAGGAAAGGAAGAAGACAATATCCAGATTTGGAGACCAAGTATGAGACCAAGAAGTT
ATCTTTAGAAAATGACATTTATGAAATAAATTTATCCCAGTGGAAGATAATGGAAAGAATTGAAA
ACCATGGCCTTAAGGGTCTCATTTTAAAAAATGATTGGGAATCCACAGGAAAAATTGAAGGACAG
GAGAGACCTCAAGAAGGATACTTCAGTAGTGTGAAAATGCCATCTGAAAAGGTGTCCTCTTACCA
GAAACGCACATCTGTTACTCCACATCAGAGACTTCATTTTGTTGATAAACCCTATGAATGTAAGG
AATGTGGGAAGGCGTTCAGAGTGCGCCAACAGCTTACTTTTCATCACAGAATTCATACTGGTGAA
AAACCGTATGAATGTAAGGAATGTGGGATGGCCTTCAGACAGACTGCACACCTTACTCGACATCA
GAGACTTCATTCTGGTGAAAAACTCTATGAATGTAAGGAATGTGGGGAAGCTTTCATATGTGGTG
CAGATCTTAGAGTACATCAGAAAATGCATATTGGTGAGAAGCCCTATGAATGTAAAGAATGTGGG
AAGGCTTTTAGGGTACGAGGACAACTTACTCTGCATCAGAGGATTCATACTGGTGAGAAACCCTA
TGTGTGTAAAGAGTGTGGAAAAGCCTTTAGACAGTACGCACACCTGACTCGGCATCAGAAGCTTA
ATAGTGCTGACAGGCTCTATGAATGCAAAGAATGTGGGAAGGCCTTTTTGTGTGGCTCTGGTCTT
AGAGTACATCACAAACTTCATACTGGTGAGAAACCCTATGAATGTAAGGAATGCGGGAAGGCCTT
TAGAGTGCGACAACAACTAACACTCCATCAGAGAATTCATACTGGTGAGAAACCCTATGAATGTA
AGGAATGTGGAAAGACCTTTAGCCGTGGTTATCATCTTATTCTCCATCACAGAATTCATACTGGT
GAAAAACCTTACGAATGTAAGGAATGCTGGAAAGCCTTTAGTCGCTACTCACAACTTATTTCACA
TCAGAGTATTCATATTGGTGTTAAGCCCTATGACTGTAAGGAATGCGGGAAGGCCTTCAGACTAC
TTTCACAACTCACACAGCATCAGAGTATTCATATTGGTGAGAAACCTTATAAATGTAAGGAATGT
GGCAAGGCCTTTAGATTGCGCCAAAAACTTACTCTACATCAGAGCATTCATACTGGCGAAAAACC
CTTTGAGTGTAAGGAATGTAGGAAGGCCTTTAGACTTAATTCATCCCTTATTCAACATCTGAGAA
TTCATTCTGGTGAGAAACCCTATGAATGTAAGGAATGTAAGAAGGCCTTTAGGCAACATTCACAC
CTTACTCATCATCTGAAAATTCATAATGTAAAAATCTAA SEQ ID NO: 4
Human ZNF545 cDNA sequence (Genbank Accession No.: NM_133466; 2635 bp)
CGTTAGGCCCCGGGGATTGTGGCGTGACCCGGCAGCGGCTTCCTCCGTTCGGGCATCGCTGTGCC
TCGGGTTCGCGCCCCGAGTGAGCAGTCCTGGCCCGGAGCGTCGGTCCTGGTAATCTGTAGGAAAA
GCGCTGCGGCCCAGGGGGTAAAGAGAGATCAGCCTCTGTGGACTCGGTGCTTCTCCTGGCAAGTA
AACCCCAAGGAGGACTGACCAGTTCTTGAATTTCTATACCATGGCCCTTCGATCAGTGATGTTCA
GTGATGTATCCATAGACTTCTCTCCAGAAGAGTGGGAATACCTGGACTTGGAACAAAAGGACTTG
TACAGAGATGTCATGTTGGAGAACTACAGCAACTTGGTCTCACTGGGATGCTTCATTTCTAAACC
AGATGTGATTTCCTCATTGGAGCAAGGAAAAGAGCCTTGGAAAGTTGTGAGGAAAGGAAGAAGAC
AATATCCAGATTTGGAGACCAAGTATGAGACCAAGAAGTTATCTTTAGAAAATGACATTTATGAA
ATAAATTTATCCCAGTGGAAGATAATGGAAAGAATTGAAACCATGGCCTTAAGGGTCTCATTTT
AAAAAATGATTGGGAATCCACAGGAAAAATTGAAGGACAGGAGAGACCTCAAGAAGGATACTTCA
GTAGTGTGAAAATGCCATCTGAAAAGGTGTCCTCTTACCAGAAACGCACATCTGTTACTCCACAT
CAGAGACTTCATTTTGTTGATAAACCCTATGAATGTAAGGAATGTGGGAAGGCGTTCAGAGTGCG
CCAACAGCTTACTTTTCATCACAGAATTCATACTGGTGAAAAACCGTATGAATGTAAGGAATGTG
```

```
GGATGGCCTTCAGACAGACTGCACACCTTACTCGACATCAGAGACTTCATTCTGGTGAAAAACTC
TATGAATGTAAGGAATGTGGGGAAGCTTTCATATGTGGTGCAGATCTTAGAGTACATCAGAAAAT
GCATATTGGTGAGAAGCCCTATGAATGTAAAGAATGTGGGAAGGCTTTTAGGGTACGAGGACAAC
TTACTCTGCATCAGAGGATTCATACTGGTGAGAAACCCTATGTGTGTAAAGAGTGTGGAAAAGCC
TTTAGACAGTACGCACACCTGACTCGGCATCAGAAGCTTAATAGTGCTGACAGGCTCTATGAATG
CAAAGAATGTGGGAAGGCCTTTTTGTGTGGCTCTGGTCTTAGAGTACATCACAAACTTCATACTG
GTGAGAAACCCTATGAATGTAAGGAATGCGGGAAGGCCTTTAGAGTGCGACAACAACTAACACTC
CATCAGAGAATTCATACTGGTGAGAAACCCTATGAATGTAAGGAATGTGGAAAGACCTTTAGCCG
TGGTTATCATCTTATTCTCCATCACAGAATTCATACTGGTGAAAAACCTTACGAATGTAAGGAAT
GCTGGAAAGCCTTTAGTCGCTACTCACAACTTATTTCACATCAGAGTATTCATATTGGTGTTAAG
CCCTATGACTGTAAGGAATGCGGGAAGGCCTTCAGACTACTTTCACAACTCACACAGCATCAGAG
TATTCATATTGGTGAGAAACCTTATAAATGTAAGGAATGTGGCAAGGCCTTTAGATTGCGCCAAA
AACTTACTCTACATCAGAGCATTCATACTGGCGAAAAACCCTTTGAGTGTAAGGAATGTAGGAAG
GCCTTTAGACTTAATTCATCCCTTATTCAACATCTGAGAATTCATTCTGGTGAGAAACCCTATGA
ATGTAAGGAATGTAAGAAGGCCTTTAGGCAACATTCACACCTTACTCATCATCTGAAAATTCATA
ATGTAAAAATCTAAGAAAGTCTTTTCAACTTCTGTGTTATAGAACATTCTATGAATGTAGTAATT
AATCTATTTTGCTCCATACATGCAACTGCGTTGGCATTAGAGGTTTTATACCATTAAAAGAGTGT
GACAATGTATTGTAGTCCATCATCACTCAAACCTGAAACTTCAGCATATTTGTTCTAAAAACTAA
TCCTGTTATAAGAATGAAAAAGACATTTACCGTCATCCCTATCCCATCACTTTGTGTCATACTGG
ACAAGACGCTTAACTGCTCTGTGCTATAATTTTTTAATTTATGACATGGTCATATAAGAGTGCAG
CAGTTTGACACACTTTCAATCAAGAGGTGGAATCTACATCCCTCTGTTGTATACAGGAATCTACA
TCCCTCTGTGACTGCTTCGCCCAGTAGAATATGGTAGACGTACTGCTGTGCTGGTTTCTTGACTC
AGACTTTACTGGTAGGGTTACTTCATCTCATGAAATGACAGAACTGTCTTGTTACAAAGTCTGGC
TACTTTGCTGAAGAGACCACATGAAGAGGCCCTGAAACTACGTAGAGAGGGAGAGGCACCTGCTG
AACCCTGTCTTCTTGACATCCACCAAGATACCAGACATTTGAGTGAAATTTTGGATCCACCAGAC
CAGCCACCAGCTAAATGCCAGTGAGCGACTTGGTAACCTGAACTGATGCCATGTAGAATGGAAGA
ATTGACCAGCTGAGCCCCTGGCCCAAATTTCTGACCCACAAAAACATGAGATATAATAAAATGGT
TGTTGTTTTAAGCCACGAAAAAAAAAAAAAAAAAA
```

SEQ ID NO: 5
Human ZNF545 protein sequence (Genbank Accession No.: NP_897723;
532amino acids)
MALRSVMFSDVSIDFSPEEWEYLDLEQKDLYRDVMLENYSNLVSLGCFISKPDVISSLEQGKEPW
KVVRKGRRQYPDLETKYETKKLSLENDIYEINLSQWKIMERIENHGLKGLILKNDWESTGKIEGQ
ERPQEGYFSSVKMPSEKVSSYQKRTSVTPHQRLHFVDKPYECKECGKAFRVRQQLTFHHRIHTGE
KPYECKECGMAFROTAHLTRHORLHSGEKLYECKECGEAFICGADLRVHOKMHIGEKPYECKECG
KAFRVRGQLTLHQRIHTGEKPYVCKECGKAFRQYAHLTRHQKLNSADRLYECKECGKAFLCGSGL
RVHHKLHTGEKPYECKECGKAFRVRQQLTLHQRIHTGEKPYECKECGKTFSRGYHLILHHRIHTG
EKPYECKECWKAFSRYSQLISHQSIHIGVKPYDCKECGKAFRLLSQLTQHQSIHIGEKPYKCKEC
GKAFRLRQKLTLHQSIHTGEKPFECKECRKAFRLNSSLIQHLRIHSGEKPYECKECKKAFRQHSH
LTHHLKIHNVKI SEQ ID NO: 6
Human ZNF545 forward primer for RT-PCR
GAGCCTTGGAAAGTTGTGAG SEQ ID NO: 7
Human ZNF545 reverse primer for RT-PCR
GGCATTTTCACACTACTGAAG SEQ ID NO: 8
Human β-actin forward primer for RT-PCR
GTCTTCCCCTCCATCGTG SEQ ID NO: 9
Human β-actin reverse primer for RT-PCR
AGGGTGAGGATGCCTCTCTT SEQ ID NO: 10
Human heterochromatin protein 1 (HP1β) forward primer for RT-PCR
TGGTAAAGGGCAAAGTGGAG SEQ ID NO: 11
Human heterochromatin protein 1 (HP1β) reverse primer for RT-PCR
GGGCAATCCAGGTTCTCTTC SEQ ID NO: 12
Human methylated ZNF545 forward primer for methylation specific PCR
(ZNF545-MSP-MF)
TTTTTTTTAGGTTTTGTCGCGTC SEQ ID NO: 13
Human methylated ZNF545 reverse primer for methylation specific PCR
(ZNF545-MSP-MR)
CTACTAAAAAAACCGAACGCG

INFORMAL SEQUENCE LISTING

SEQ ID NO: 14
Human unmethylated ZNF545 forward primer for methylation specific PCR
(ZNF545-MSP-UF)
TTTTTTTTTAGGTTTTGTTGTGTT SEQ ID NO: 15
Human unmethylated ZNF545 reverse primer for methylation specific PCR
(ZNF545-MSP-UR)
CCAAACACACTCACAAATACA SEQ ID NO: 16
Human ZNF545 forward primer for bisulfite genomic sequencing
(ZNF545-BGS-F)
GTATAGGGTTTTTAGTTGGTAT SEQ ID NO: 17
Human ZNF545 reverse primer for bisulfite genomic sequencing
(ZNF545-BGS-R)
CCTCTCTCTTTACCCCCTAA SEQ ID NO: 18
Human ZNF545 small interfering RNA (sense strand)
CCGUGGUUAUCAUCUUAUU dTdT SEQ ID NO: 19
Human ZNF545 small interfering RNA (antisense strand)
dTdTGGCACCAAUAGUAGAAUAA SEQ ID NO: 20
Human ribosomal DNA (rDNA) forward primer for PCR
CCCGGGGGAGGTATATCTTT SEQ ID NO: 21
Human ribosomal DNA (rDNA) reverse primer for PCR
GACGTCACCACATCGATCAC SEQ ID NO: 22
Human heterochromatin protein 1 (HP1β) small interfering RNA (sense strand)
GGAAGGGAUUCUCAGAUGAdTdT SEQ ID NO: 23
Human heterochromatin protein 1 (HP1β) small interfering RNA (antisense strand)
dTdT CCUUCCCUAAGAGUCUACU SEQ ID NO: 24
Human rDNA forward primer for ChIP-PCR
CCCGGGGGAGGTATATCTTT SEQ ID NO: 25
Human rDNA reverse primer for ChIP-PCR
CCAACCTCTCCGACGACA

What is claimed is:

1. A method for assessing time of survival from gastric cancer in a subject suffering from gastric cancer, comprising the steps of:
   (a) detecting methylation in a promoter region of the ZNF545 gene corresponding to SEQ ID NO: 1 or 2 by:
      (i) treating genomic DNA of a sample taken from the subject with a bisulfite, wherein the sample is taken from non-cancer tissue adjacent to the gastric cancer;
      (ii) amplifying the treated genomic DNA by performing a polymerase chain reaction (PCR) with a primer selected from the group consisting of SEQ ID NOs: 12, 13, 16, and 17;
      (iii) detecting in the amplified DNA after stop (b) a methylated version of the promoter region of the ZNF545 gene; and
   (b) determining the subject as having a shorter time of survival when a methylated version of the genomic DNA sequence is detected in the sample, in comparison to another subject suffering from gastric cancer but whose non-cancer tissue adjacent to gastric cancer is determined to contain no methylated version of the promoter region of the ZNF545 gene.

2. The method of claim 1, wherein step (iii) comprises sequencing of the DNA amplified from step (ii).

3. The method of claim 1, wherein the subject suffers from stage I or stage II gastric cancer.

4. The method of claim 1, wherein the time of survival is over a time period of 1-12 years.

5. The method of claim 1, wherein the bisulfite is sodium bisulfite.

* * * * *